(12) United States Patent
Anderson et al.

(10) Patent No.: US 11,723,518 B2
(45) Date of Patent: Aug. 15, 2023

(54) DIRECT VISUALIZATION CATHETER AND SYSTEM

(71) Applicants: Boston Scientific Scimed inc., Maple Grove, MN (US); Mayo Foundation for Medical Education and Research, Rochester, MN (US)

(72) Inventors: James M. Anderson, Corcoran, MN (US); Adam D. Grovender, Maple Grove, MN (US); Eric M. Petersen, Maple Grove, MN (US); David Raab, Roseville, MN (US); Mark S. Smith, Coon Rapids, MN (US); Cass A. Hanson, St. Paul, MN (US); Timothy A. Ostroot, Cokato, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 932 days.

(21) Appl. No.: 16/169,752

(22) Filed: Oct. 24, 2018

(65) Prior Publication Data

US 2019/0117044 A1 Apr. 25, 2019

Related U.S. Application Data

(60) Provisional application No. 62/577,159, filed on Oct. 25, 2017, provisional application No. 62/577,163, filed on Oct. 25, 2017.

(51) Int. Cl.
*A61B 1/00* (2006.01)
*A61B 1/05* (2006.01)
(Continued)

(52) U.S. Cl.
CPC ...... *A61B 1/00082* (2013.01); *A61B 1/00183* (2013.01); *A61B 1/05* (2013.01);
(Continued)

(58) Field of Classification Search
CPC ... A61B 1/00082; A61B 1/05; A61B 1/00183; A61B 1/051; A61B 90/36; A61B 1/018;
(Continued)

(56) References Cited

U.S. PATENT DOCUMENTS 3,162,190 A * 12/1964 Del Gizzo Giovanni .................. A61B 1/00177
600/123
3,690,769 A * 9/1972 Mori ..................... A61B 5/1459
600/116
(Continued)

FOREIGN PATENT DOCUMENTS

JP 2006-334397 A 12/2006
JP 2012-200597 A 10/2012
(Continued)

OTHER PUBLICATIONS

International Search Report and Written Opinion received for PCT Patent Application No. PCT/US2018/057346, dated Feb. 11, 2019, 10 pages.

*Primary Examiner* — Ryan N Henderson
(74) *Attorney, Agent, or Firm* — Seager, Tufte & Wickhem, LLP

(57) ABSTRACT

A direct visualization catheter includes a handle, a balloon, an elongate shaft, and a camera assembly. The elongate shaft has a proximal end and a distal end opposite the proximal end. The proximal end is coupled to the handle. The distal end is coupled to the balloon and defines a longitudinal axis. The camera assembly is coupled to the distal end of the elongate shaft and is disposed within the balloon. The camera assembly includes a camera and an adjustment mechanism for varying a configuration of the camera relative to the distal end of the elongate shaft between a delivery configuration and a deployed configuration. The camera faces primarily in a radial direction in the delivery configu- (Continued)

ration and the camera faces primarily in an axial direction in the deployed configuration.

13 Claims, 11 Drawing Sheets

(51) Int. Cl.
    *A61B 1/018*     (2006.01)
    *A61B 1/06*     (2006.01)

(52) U.S. Cl.
    CPC .............. *A61B 1/051* (2013.01); *A61B 1/018* (2013.01); *A61B 1/06* (2013.01)

(58) Field of Classification Search
    CPC ... A61B 1/06; A61B 1/00174; A61B 1/00177; A61B 1/00179; A61B 1/00181; A61B 1/0008; A61B 1/00087; A61B 1/00089; A61B 1/00096; A61B 1/32; A61B 18/24; A61B 18/245; A61B 18/22; A61B 18/1492; A61M 25/0102; A61M 29/00; A61M 25/1002; A61M 25/10; A61M 25/104; A61M 25/0125
    See application file for complete search history.

(56) References Cited

U.S. PATENT DOCUMENTS

| | | | | |
|---|---|---|---|---|
| 4,224,929 A * | 9/1980 | Furihata | ............. | A61B 1/00098 600/116 |
| 4,470,407 A * | 9/1984 | Hussein | ................. | A61B 18/24 600/116 |
| 4,619,247 A * | 10/1986 | Inoue | ..................... | B05B 11/06 600/116 |
| 4,681,093 A * | 7/1987 | Ono | ................... | A61B 1/00082 600/116 |
| 4,708,434 A * | 11/1987 | Tsuno | ................ | A61B 1/00082 600/116 |
| 4,717,387 A * | 1/1988 | Inoue | ..................... | A61B 1/018 604/264 |
| 4,779,611 A * | 10/1988 | Grooters | ............ | A61B 1/00082 600/116 |
| 4,784,133 A * | 11/1988 | Mackin | ................ | A61B 1/3137 606/7 |
| 4,830,460 A * | 5/1989 | Goldenberg | ....... | A61B 1/00165 606/7 |
| 4,929,246 A * | 5/1990 | Sinofsky | ............ | A61B 17/0057 606/8 |
| 4,961,738 A * | 10/1990 | Mackin | ................ | A61B 1/00082 600/116 |
| 4,976,710 A * | 12/1990 | Mackin | ................. | A61B 1/018 604/917 |
| 5,029,574 A * | 7/1991 | Shimamura | ........ | A61B 1/00082 600/116 |
| 5,409,483 A * | 4/1995 | Campbell | ............ | A61N 5/0601 606/15 |
| 5,458,612 A * | 10/1995 | Chin | .................. | A61B 1/00082 606/192 |
| 6,036,685 A * | 3/2000 | Mueller | ................. | A61B 1/018 606/7 |
| 6,134,460 A * | 10/2000 | Chance | ............. | G01N 21/3151 600/344 |
| 6,692,430 B2 * | 2/2004 | Adler | .................... | A61B 1/0655 977/869 |
| 6,979,290 B2 * | 12/2005 | Mourlas | ............. | A61B 1/00082 600/116 |
| 7,112,195 B2 * | 9/2006 | Boll | ........................ | A61B 18/24 606/2 |
| 7,186,214 B2 * | 3/2007 | Ness | ................. | A61B 17/3421 600/116 |
| 7,534,204 B2 * | 5/2009 | Starksen | .......... | A61B 17/00234 600/116 |
| 7,537,580 B2 * | 5/2009 | Willard | ................. | A61M 25/10 604/96.01 |
| 8,016,748 B2 * | 9/2011 | Mourlas | ............. | A61B 1/00096 600/116 |
| 8,050,746 B2 * | 11/2011 | Saadat | ................. | A61B 1/0008 600/478 |
| 8,078,266 B2 * | 12/2011 | Saadat | ............... | A61B 1/00089 600/478 |
| 8,123,722 B2 * | 2/2012 | Chang | ................ | A61B 17/1204 600/101 |
| 8,131,350 B2 * | 3/2012 | Saadat | .................... | A61B 1/05 600/478 |
| 8,172,747 B2 * | 5/2012 | Wallace | ............... | A61B 5/0084 600/478 |
| 8,709,008 B2 * | 4/2014 | Willis | ................ | A61B 18/1492 606/41 |
| 9,610,006 B2 | 4/2017 | Salahieh et al. | | |
| 2001/0007937 A1 * | 7/2001 | MacKin | ................. | A61B 18/24 604/20 |
| 2001/0020126 A1 * | 9/2001 | Swanson | ................ | A61B 8/445 600/478 |
| 2002/0042555 A1 * | 4/2002 | Komachi | ........... | A61B 1/00177 600/177 |
| 2002/0111548 A1 * | 8/2002 | Swanson | ............. | A61B 5/0036 600/478 |
| 2002/0188204 A1 * | 12/2002 | McNamara | ........ | A61B 1/00183 600/478 |
| 2003/0050632 A1 * | 3/2003 | Fjield | ................. | A61B 18/1492 606/27 |
| 2004/0015052 A1 * | 1/2004 | Barthel | ............. | A61B 1/00096 600/116 |
| 2004/0097788 A1 * | 5/2004 | Mourlas | ................. | A61B 1/005 600/116 |
| 2004/0210278 A1 * | 10/2004 | Boll | ........................ | A61B 18/24 607/89 |
| 2005/0119523 A1 * | 6/2005 | Starksen | .......... | A61B 17/00234 606/1 |
| 2005/0182465 A1 * | 8/2005 | Ness | ................. | A61B 17/3421 607/116 |
| 2005/0197530 A1 * | 9/2005 | Wallace | ............... | A61B 5/0084 600/116 |
| 2005/0228452 A1 * | 10/2005 | Mourlas | ............ | A61M 25/1002 606/41 |
| 2005/0272977 A1 | 12/2005 | Saadat et al. | | |
| 2006/0084839 A1 * | 4/2006 | Mourlas | ............. | A61B 1/00082 600/116 |
| 2007/0015964 A1 * | 1/2007 | Eversull | ................. | A61B 1/005 600/114 |
| 2007/0016130 A1 * | 1/2007 | Leeflang | ........... | A61M 25/0105 604/95.04 |
| 2007/0083217 A1 * | 4/2007 | Eversull | ................ | A61M 25/09 606/114 |
| 2007/0161855 A1 * | 7/2007 | Mikkaichi | ............... | A61B 1/041 600/113 |
| 2007/0293724 A1 * | 12/2007 | Saadat | ............... | A61B 1/00085 600/156 |
| 2008/0009747 A1 * | 1/2008 | Saadat | .................... | A61B 1/015 604/510 |
| 2008/0015445 A1 * | 1/2008 | Saadat | ................. | A61B 1/0008 600/470 |
| 2008/0015569 A1 * | 1/2008 | Saadat | ............... | A61B 1/00085 606/41 |
| 2008/0027464 A1 * | 1/2008 | Moll | ....................... | A61B 34/30 606/130 |
| 2008/0058591 A1 * | 3/2008 | Saadat | .................... | A61B 1/015 600/109 |
| 2008/0058650 A1 * | 3/2008 | Saadat | ................... | A61B 1/042 600/478 |
| 2008/0183036 A1 * | 7/2008 | Saadat | ................. | A61B 1/3137 606/41 |
| 2008/0188759 A1 * | 8/2008 | Saadat | ............... | A61B 1/00147 600/478 |
| 2008/0214889 A1 * | 9/2008 | Saadat | ............... | A61B 1/00089 606/205 |
| 2008/0275300 A1 * | 11/2008 | Rothe | ...................... | A61B 1/01 600/129 |

(56) References Cited

U.S. PATENT DOCUMENTS

| | | | |
|---|---|---|---|
| 2009/0030412 A1* | 1/2009 | Willis | A61B 1/00089 606/41 |
| 2009/0076498 A1* | 3/2009 | Saadat | A61B 18/1492 606/41 |
| 2009/0082623 A1* | 3/2009 | Rothe | A61B 1/3137 600/109 |
| 2009/0143640 A1* | 6/2009 | Saadat | A61B 1/00089 606/41 |
| 2009/0227999 A1* | 9/2009 | Willis | A61B 1/00089 606/41 |
| 2009/0275799 A1* | 11/2009 | Saadat | A61B 1/04 600/109 |
| 2009/0275842 A1* | 11/2009 | Saadat | A61B 1/05 600/478 |
| 2009/0299363 A1* | 12/2009 | Saadat | A61B 1/00085 606/41 |
| 2010/0004633 A1* | 1/2010 | Rothe | A61M 25/0136 604/528 |
| 2010/0010311 A1* | 1/2010 | Miller | A61B 1/00082 600/156 |
| 2010/0094081 A1* | 4/2010 | Rothe | A61B 1/00089 600/104 |
| 2010/0198005 A1* | 8/2010 | Fox | A61B 17/3415 604/164.1 |
| 2010/0292558 A1* | 11/2010 | Saadat | A61B 1/00089 600/407 |
| 2011/0034790 A1* | 2/2011 | Mourlas | A61B 1/005 604/20 |
| 2011/0137117 A1* | 6/2011 | Jacobsen | A61B 1/05 600/109 |
| 2011/0144576 A1* | 6/2011 | Rothe | A61B 1/00042 604/95.04 |
| 2011/0301417 A1* | 12/2011 | Mourlas | A61B 1/005 600/116 |
| 2011/0306833 A1* | 12/2011 | Saadat | A61B 1/32 600/109 |
| 2012/0004577 A1* | 1/2012 | Saadat | A61B 1/005 600/587 |
| 2013/0172726 A9 | 7/2013 | Saadat et al. | |
| 2014/0238175 A1 | 8/2014 | Huszar et al. | |
| 2016/0106308 A1 | 4/2016 | Field | |
| 2017/0042615 A1 | 2/2017 | Salahieh et al. | |
| 2017/0079519 A1 | 3/2017 | Sung et al. | |
| 2017/0296793 A1 | 10/2017 | Anderson et al. | |
| 2017/0296795 A1 | 10/2017 | Troutman et al. | |

FOREIGN PATENT DOCUMENTS

| | | |
|---|---|---|
| JP | 2014-530644 A | 11/2014 |
| JP | 2016-522051 A | 7/2016 |
| WO | 2013/073061 A1 | 5/2013 |
| WO | 2016/044320 A1 | 3/2016 |
| WO | 2017/087549 A1 | 5/2017 |
| WO | 2017/106698 A1 | 6/2017 |

* cited by examiner

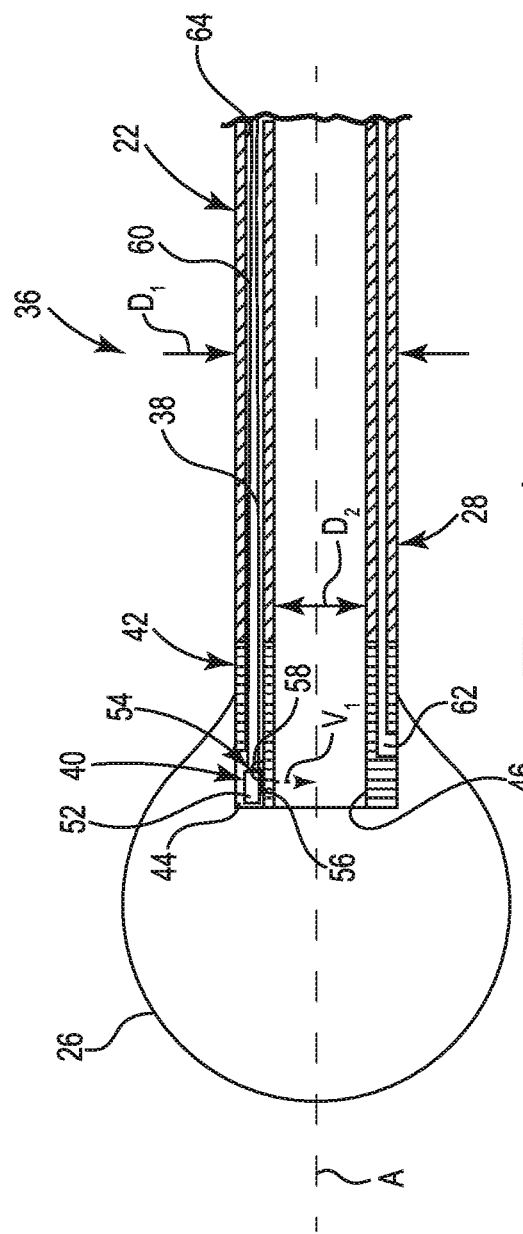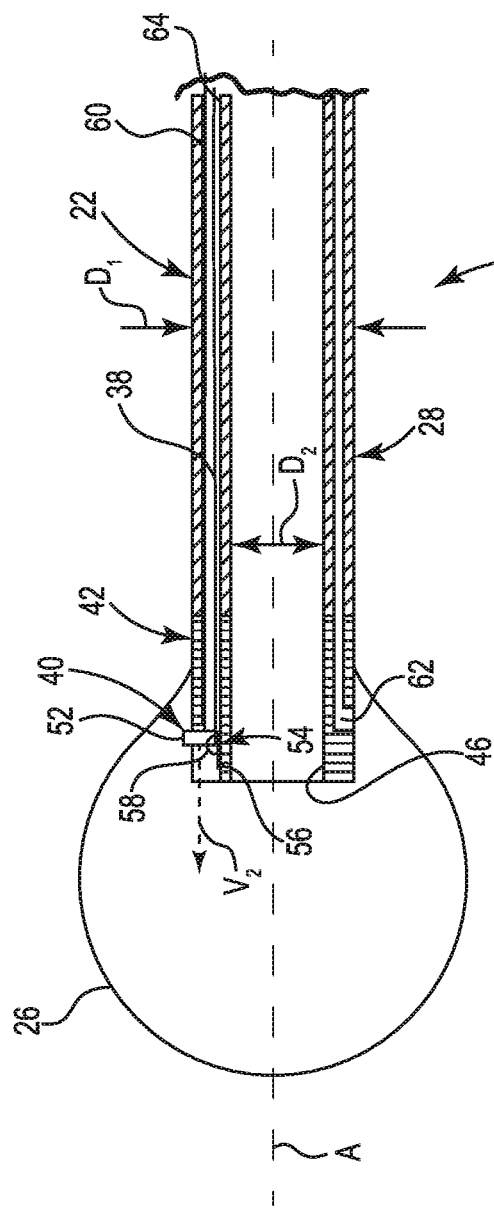

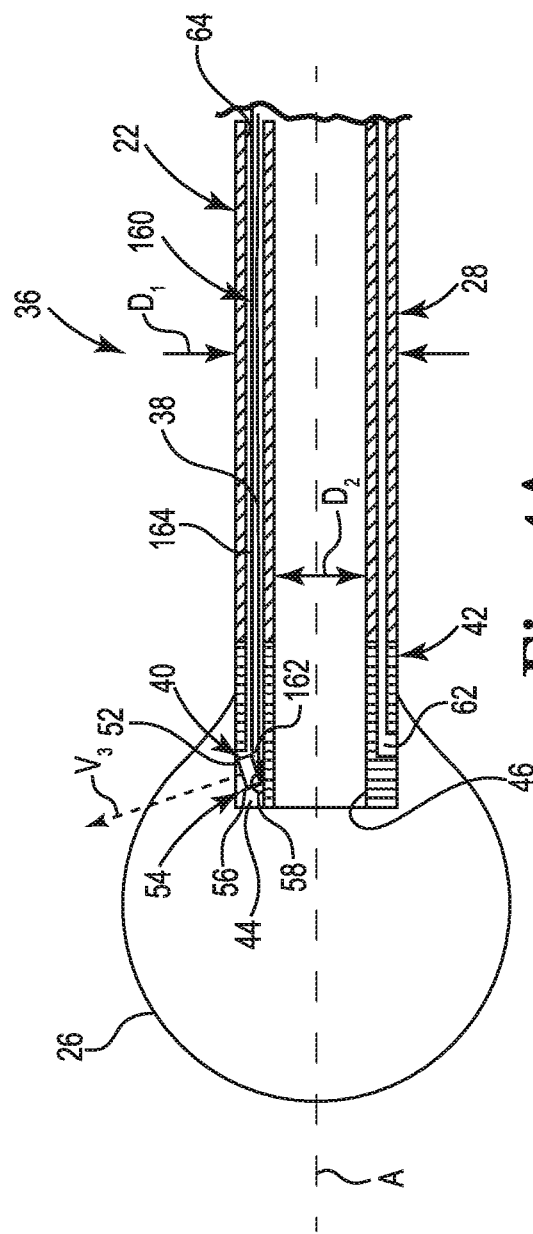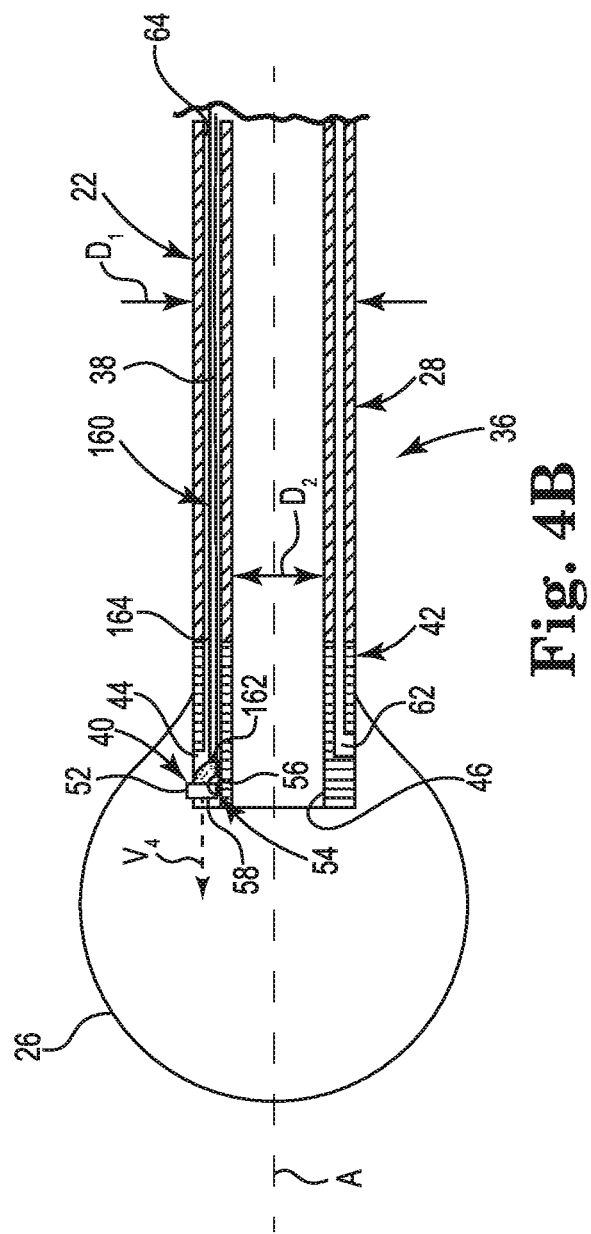

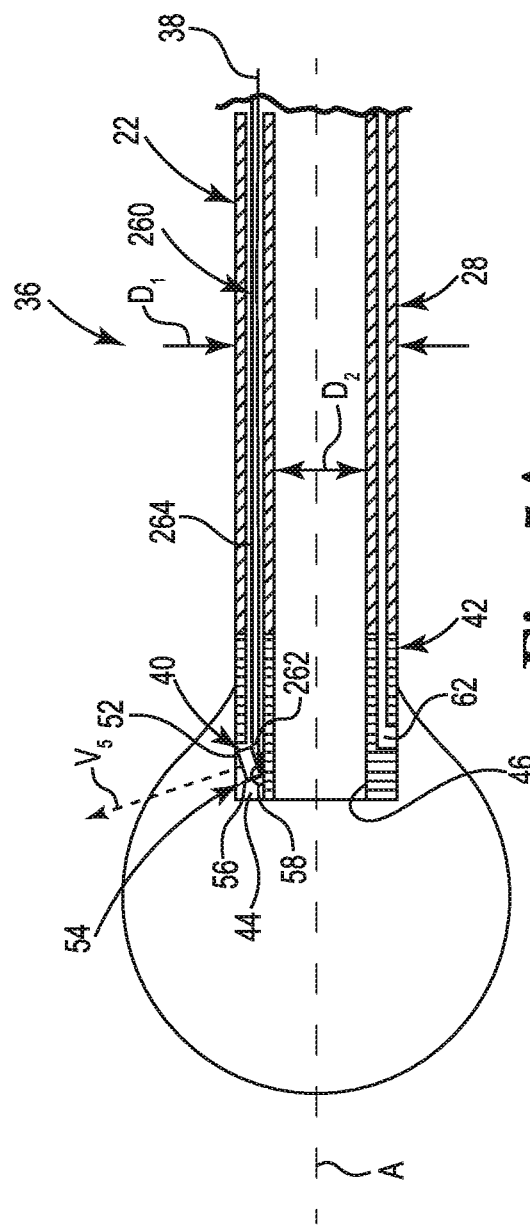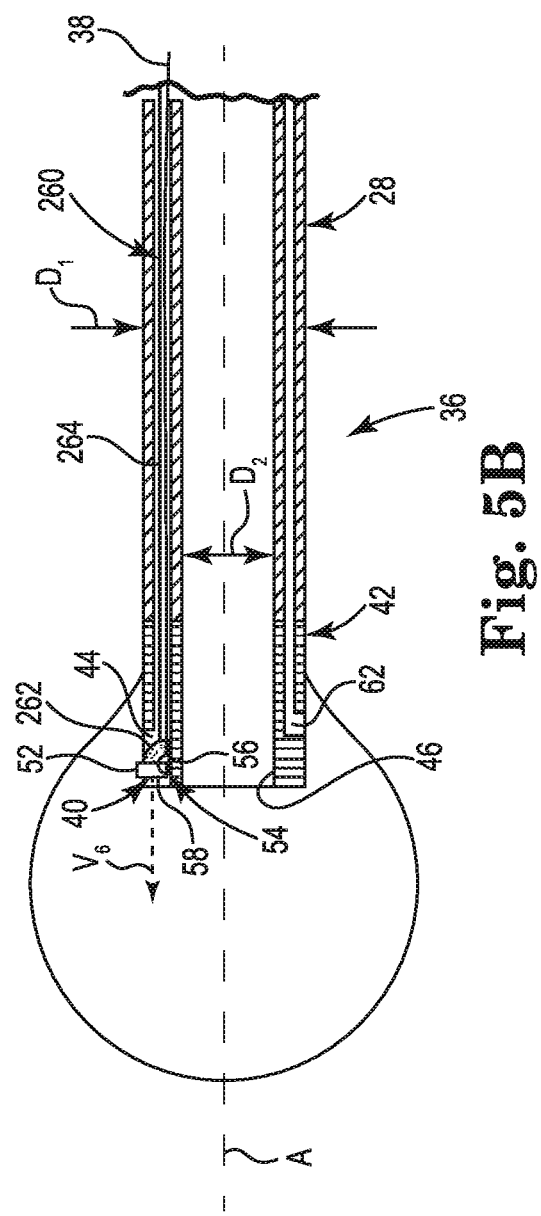

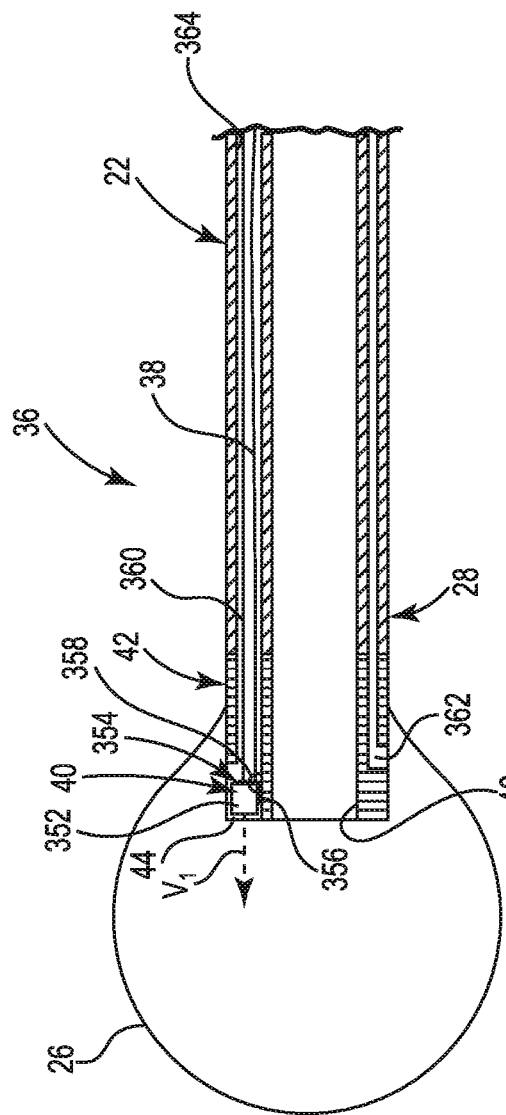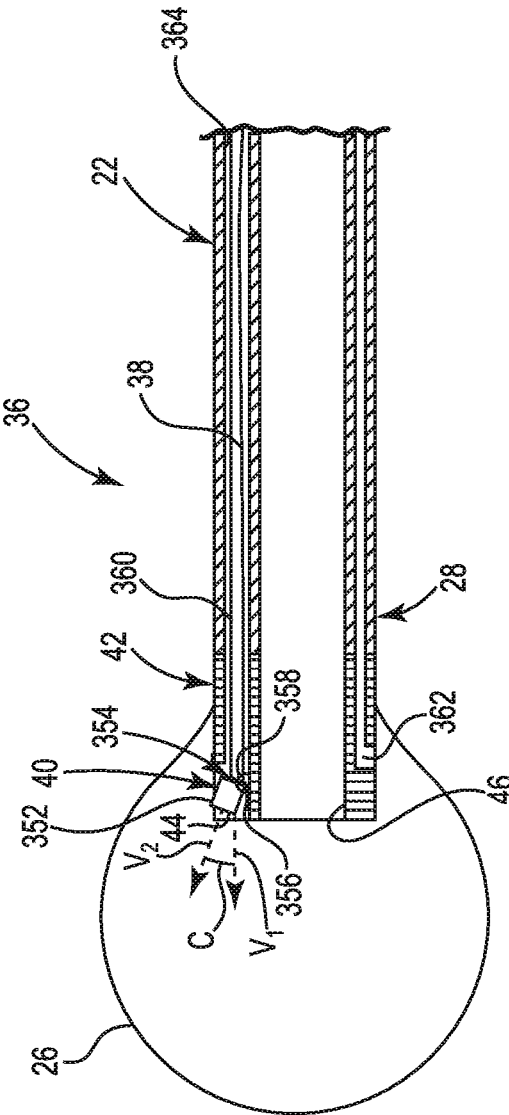

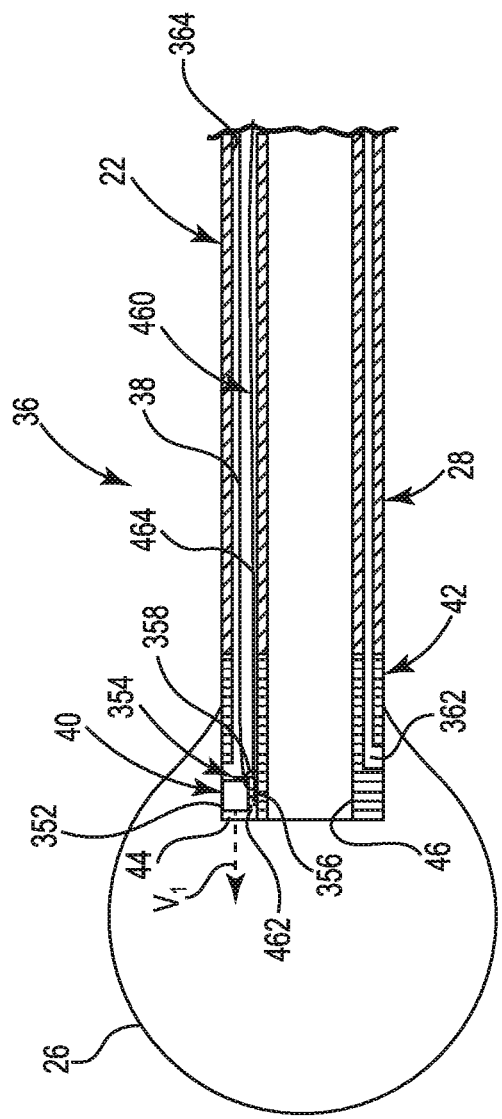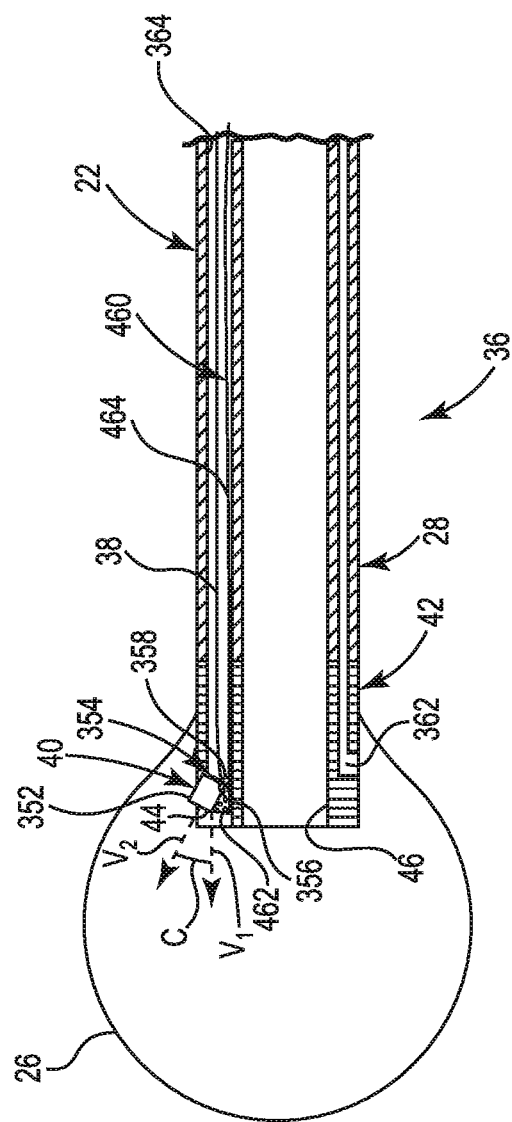

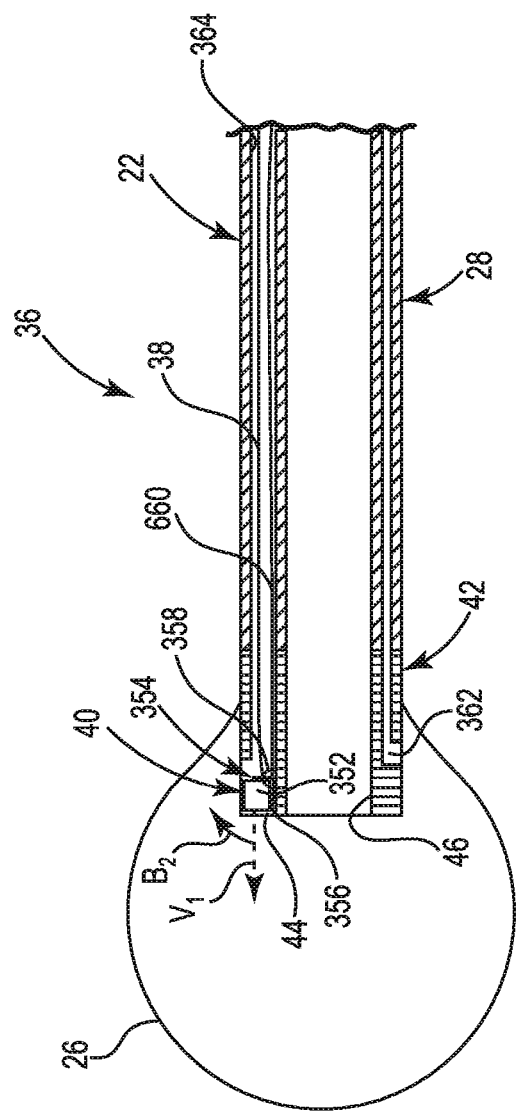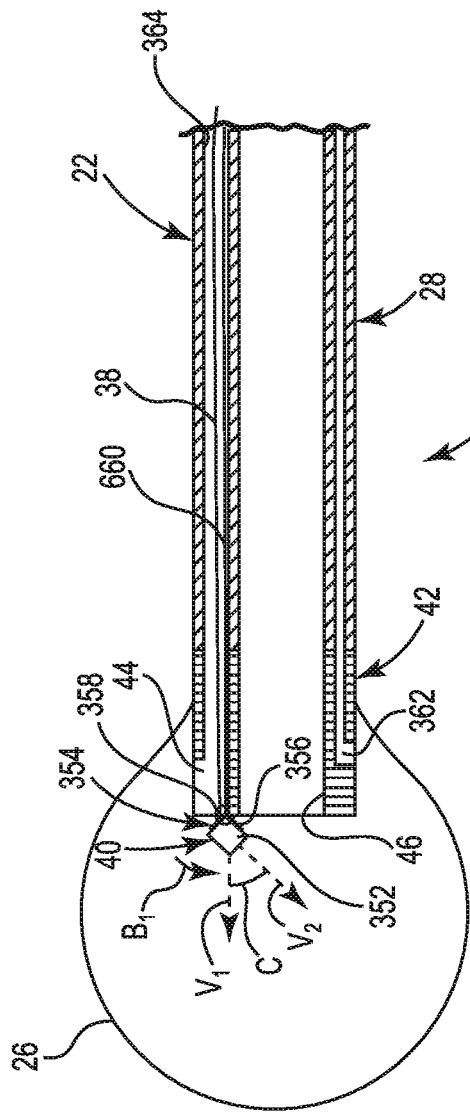

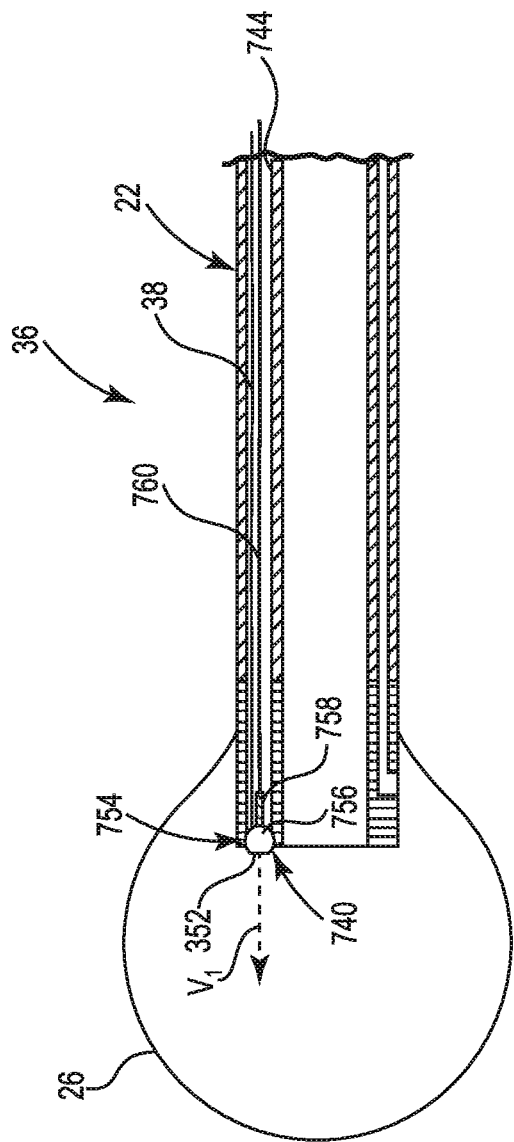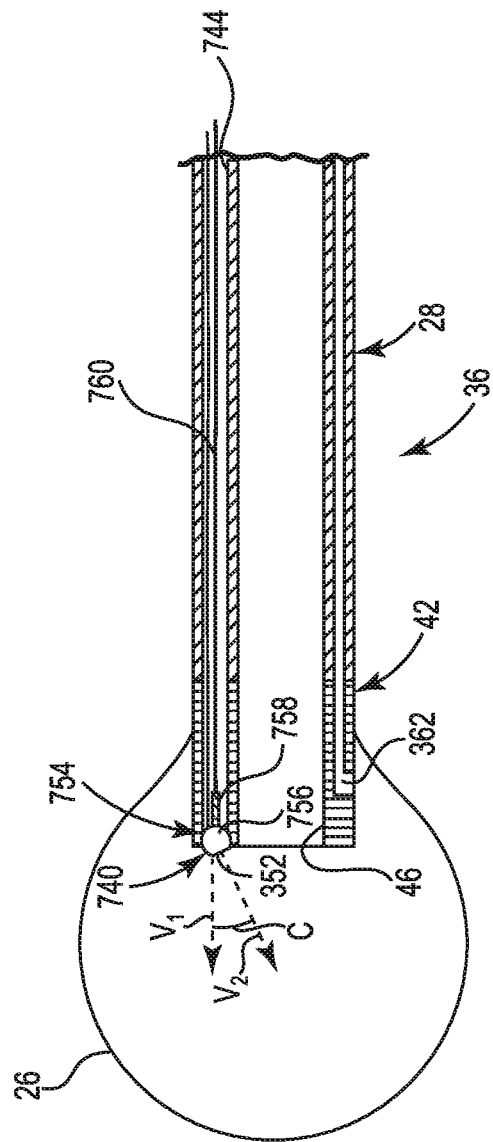

DIRECT VISUALIZATION CATHETER AND SYSTEM

CROSS-REFERENCE TO RELATED APPLICATION

This application claims priority to Provisional Application Nos. 62/577,159, filed Oct. 25, 2017, and 62/577,163, filed Oct. 25, 2017, all of which are herein incorporated by reference in their entireties.

TECHNICAL FIELD

The present disclosure relates to medical devices and methods for direct visualization within a body. More specifically, the disclosure relates to catheters, systems, and methods for direct visualization within a blood pool in a minimally-invasive manner.

BACKGROUND

Direct visualization of tissues within a patient can provide important information and guidance in the diagnosis and treatment of illnesses. With respect to heart diseases, direct visualization can be helpful, for example, in the diagnosis and treatment heart valve diseases, among other diseases. In vivo images provided by direct visualization can allow for a thorough inspection of tissues with higher resolution than other techniques, such as ultrasound. Procedures, such as a septal cross, mitral valve repair, and stitching of a valve annulus can all benefit from the accuracy provided by direct visualization.

Direct visualization within the heart is challenging because the general opacity of blood can obscure the tissues to be viewed. Some direct visualization catheters employ a transparent balloon at the end of the catheter to displace blood adjacent to the tissues to be viewed. The balloon can be filled with saline and provide an optical lensing effect, further clarifying the view of a camera within the balloon at the end of the catheter.

SUMMARY

Example 1 is a direct visualization catheter including a handle, a balloon, an elongate shaft, and a camera assembly. The elongate shaft has a proximal end and a distal end opposite the proximal end. The proximal end is coupled to the handle. The distal end is coupled to the balloon and defines a longitudinal axis. The camera assembly is coupled to the distal end of the elongate shaft and is disposed within the balloon. The camera assembly includes a camera and an adjustment mechanism for varying a configuration of the camera relative to the distal end of the elongate shaft between a delivery configuration and a deployed configuration. The camera faces primarily in a radial direction in the delivery configuration and the camera faces primarily in an axial direction in the deployed configuration.

Example 2 is the direct visualization catheter of Example 1, wherein in the delivery configuration, the camera does not extend radially beyond the elongate shaft, and in the deployed configuration, the camera extends radially beyond the elongate shaft.

Example 3 is the direct visualization catheter of either of Examples 1 or 2, wherein the elongate shaft has a diameter from 3.1 mm to 3.5 mm, the elongate shaft further including a lumen extending from the proximal end to the distal end, the lumen having a lumen diameter from 2.2 mm to 2.5 mm.

Example 4 is the direct visualization catheter of any of Examples 1-3, wherein the adjustment mechanism includes a hinge, a biasing element, and a control element. The hinge couples the camera to the distal end of the elongate shaft. The hinge is configured to permit the camera to move relative to the distal end of the elongate shaft. The biasing element is configured apply a first force about the hinge. The control element is configured apply a second force about the hinge opposite the first force.

Example 5 is the direct visualization catheter of Example 4, wherein the control element includes an actuation thread extending to the handle, the actuation thread coupled to the camera.

Example 6 is the direct visualization catheter of Example 4, wherein the control element includes an inflatable device disposed between the distal end of the elongate shaft and the camera, the inflatable device in fluid communication with a pressurized control lumen extending to the handle.

Example 7 is the direct visualization catheter of Example 4, wherein the control element includes an electroactive element disposed between the distal end of the elongate shaft and the camera, the electroactive element in electrical communication with a plurality of control wires extending to the handle.

Example 8 is the direct visualization catheter of any of Examples 4-7, wherein the hinge includes a plurality of electrical conductors configured to electrically connect the camera to electrical lines to be electrically connected to an image processing device for at least one of: image storage, image display, and image analysis.

Example 9 is a system for direct visualization within a blood pool, the system including an image processing device and the direct visualization catheter according to any of Example 1-8 electrically connected to the image processing device.

Example 10 is a system for direct visualization within a blood pool. The system includes an image processing device and a direct visualization catheter electrically connected to the image processing device. The direct visualization catheter includes a handle, a transparent balloon, an elongate shaft, and a camera assembly. The elongate shaft has a proximal end and a distal end opposite the proximal end. The proximal end is coupled to the handle. The distal end is coupled to the balloon and defines a longitudinal axis. The elongate shaft includes a plurality of lumens extending from the proximal end to the distal end. The camera assembly is coupled the distal end of the elongate shaft and disposed within the balloon. The camera assembly includes a camera, a hinge connecting the camera to the elongate shaft at the distal end of the elongate shaft, a biasing element configured to apply a first force about the hinge, and a control element configured to apply a second force about the hinge opposite the first force to vary a configuration of the camera relative to the distal end of the elongate shaft between a delivery configuration and a deployed configuration. The camera faces primarily in a radial direction in the delivery configuration and the camera faces primarily in an axial direction in the deployed configuration.

Example 11 is the system of Example 10, wherein the control element includes an actuation thread and a position switch. The actuation thread extends through one of the plurality of lumens. The position switch is disposed within the handle. The actuation thread physically connects the camera to the position switch.

Example 12 is the system of Example 10, wherein the control element includes an inflatable device and a pressure regulating device. The inflatable device is disposed between the elongate shaft and the camera. One of the plurality of lumens fluidly connects the inflatable device and the pressure regulating device.

Example 13 is the system of Example 10, wherein the control element includes an electroactive element disposed between the elongate shaft and the camera, a voltage regulating device, and control wires extending through at least one of the plurality of lumens. The control wires electrically connect the electroactive element to the voltage regulating device.

Example 14 is the system of any of Examples 10-13, wherein the hinge includes a plurality of electrical conductors configured to electrically connect the camera to electrical lines electrically connected to the image processing device for at least one of: image storage, image display, and image analysis.

Example 15 is the system of any of Examples 10-14, wherein the elongate shaft has a diameter from 3.1 mm to 3.5 mm and one of the plurality of lumens has a lumen diameter from 2.2 mm to 2.5 mm.

Example 16 is a direct visualization catheter including a handle, a balloon, an elongate shaft, and a camera assembly. The elongate shaft has a proximal end and a distal end opposite the proximal end. The proximal end is coupled to the handle. The distal end is coupled to the balloon and defines a longitudinal axis. The camera assembly is coupled to the distal end of the elongate shaft and is disposed within the balloon. The camera assembly includes a camera and an adjustment mechanism for varying a configuration of the camera relative to the distal end of the elongate shaft between a delivery configuration and a deployed configuration. The camera faces primarily in a radial direction in the delivery configuration and the camera faces primarily in an axial direction in the deployed configuration.

Example 17 is the direct visualization catheter of Example 16, wherein in the delivery configuration, the camera does not extend radially beyond the elongate shaft, and in the deployed configuration, the camera extends radially beyond the elongate shaft.

Example 18 is the direct visualization catheter of either of Examples 16 or 17, wherein the elongate shaft has a diameter from 3.1 mm to 3.5 mm and the elongate shaft further includes a lumen extending from the proximal end to the distal end, the lumen having a lumen diameter from 2.2 mm to 2.5 mm.

Example 19 is the direct visualization catheter of any of Examples 16-18, wherein the adjustment mechanism includes a hinge, a biasing element, and a control element. The hinge couples the camera to the distal end of the elongate shaft. The hinge is configured to permit the camera to move relative to the distal end of the elongate shaft. The biasing element is configured apply a first force about the hinge. The control element is configured apply a second force about the hinge opposite the first force.

Example 20 is the direct visualization catheter of Example 19, wherein the control element includes an actuation thread extending to the handle, the actuation thread coupled to the camera.

Example 21 is the direct visualization catheter of Example 19, wherein the control element includes an inflatable device disposed between the distal end of the elongate shaft and the camera, the inflatable device in fluid communication with a pressurized control lumen extending to the handle.

Example 22 is the direct visualization catheter of Example 19, wherein the control element includes an electroactive element disposed between the distal end of the elongate shaft and the camera, the electroactive element in electrical communication with a plurality of control wires extending to the handle.

Example 23 is the direct visualization catheter of any of Examples 19-22, wherein the hinge includes a plurality of electrical conductors configured to electrically connect the camera to electrical lines to be electrically connected to an image processing device for at least one of: image storage, image display, and image analysis.

Example 24 is a system for direct visualization within a blood pool. The system includes an image processing device and a direct visualization catheter electrically connected to the image processing device. The direct visualization catheter includes a handle, a transparent balloon, an elongate shaft, and a camera assembly. The elongate shaft has a proximal end and a distal end opposite the proximal end. The proximal end is coupled to the handle. The distal end is coupled to the balloon and defines a longitudinal axis. The elongate shaft includes a plurality of lumens extending from the proximal end to the distal end. The camera assembly is coupled the distal end of the elongate shaft and disposed within the balloon. The camera assembly includes a camera, a hinge connecting the camera to the elongate shaft at the distal end of the elongate shaft, a biasing element configured to apply a first force about the hinge, and a control element configured to apply a second force about the hinge opposite the first force to vary a configuration of the camera relative to the distal end of the elongate shaft between a delivery configuration and a deployed configuration. The camera faces primarily in a radial direction in the delivery configuration and the camera faces primarily in an axial direction in the deployed configuration.

Example 25 is the system of Example 24, wherein the control element includes an actuation thread extending through one of the plurality of lumens, and a position switch disposed within the handle. The actuation thread physically connects the camera to the position switch.

Example 26 is the system of Example 24, wherein the control element includes an inflatable device and a pressure regulating device. The inflatable device is disposed between the elongate shaft and the camera. One of the plurality of lumens fluidly connects the inflatable device and the pressure regulating device.

Example 27 is the system of Example 24, wherein the control element includes an electroactive element, a voltage regulating device, and control wires. The electroactive element is disposed between the elongate shaft and the camera. The control wires extend through at least one of the plurality of lumens. The control wires electrically connect the electroactive element to the voltage regulating device.

Example 28 is the system of any of Examples 24-27, wherein the hinge includes a plurality of electrical conductors configured to electrically connect the camera to electrical lines electrically connected to the image processing device for at least one of: image storage, image display, and image analysis.

Example 29 is the system of any of Examples 24-28, wherein in the delivery configuration, the camera does not extend radially beyond the elongate shaft, and in the deployed configuration, the camera extends radially beyond the elongate shaft.

Example 30 is the system of any of Examples 24-29, wherein the elongate shaft has a diameter from 3.1 mm to 3.5 mm and one of the plurality of lumens has a lumen diameter from 2.2 mm to 2.5 mm.

Example 31 is a method for visualizing tissue within a body. The method includes inserting a catheter within the body, inflating a transparent balloon at a distal end of the catheter, adjusting a configuration of a camera between a delivery configuration and a deployed configuration, and contacting the tissue to be visualized with a portion of the inflated balloon. The catheter has a proximal end opposite the distal end. The distal end defines a longitudinal axis. The camera facing primarily in a radial direction in the delivery configuration and the camera facing primarily in an axial direction in the deployed configuration. The camera is connected to the distal end of the catheter and is disposed within the transparent balloon.

Example 32 is the method of Example 31, wherein adjusting the configuration of the camera between the delivery configuration and the deployed configuration includes pulling an actuation thread connected to the camera to move the camera about a hinge connecting the camera to the catheter.

Example 33 is the method of Example 31, wherein adjusting the configuration of the camera between the delivery configuration and the deployed configuration includes inflating an inflatable device disposed between the camera and the catheter.

Example 34 is the method of Example 31, wherein adjusting the configuration of the camera between the delivery configuration and the deployed configuration includes varying a voltage applied to an electroactive material disposed between the camera and the catheter to move the camera about a hinge connecting the camera to the catheter.

Example 35 is the method of any of Examples 31-34, wherein in the delivery configuration, the camera does not extend radially beyond the catheter, and in the deployed configuration, the camera extends radially beyond the catheter.

Example 36 is a direct visualization catheter including a balloon, an elongate shaft, and a camera assembly coupled to the distal end of the elongate shaft and disposed within the balloon. The elongate shaft has a proximal end and a distal end opposite the proximal end. The distal end is coupled to the balloon. The camera assembly includes a camera and an adjustment mechanism configured to vary a viewing direction observed by the camera relative to the distal end of the elongate shaft.

Example 37 is the direct visualization catheter of Example 36, wherein the adjustment mechanism includes a hinge coupling the camera to the distal end of the elongate shaft, a biasing element configured to apply a first force about the hinge, and a control element configured to selectively apply a second force about the hinge opposite the first force. The hinge is configured to permit the camera to move relative to the distal end of the elongate shaft.

Example 38 is the direct visualization catheter of Example 37, wherein the control element includes an actuation thread extending to the proximal end, the actuation thread coupled to the camera.

Example 39 is the direct visualization catheter of Example 37, wherein the control element includes an inflatable device disposed between the distal end of the elongate shaft and the camera, the inflatable device in fluid communication with a pressurized control lumen extending to the proximal end.

Example 40 is the direct visualization catheter of Example 37, wherein the control element includes an electroactive element disposed between the distal end of the elongate shaft and the camera, the electroactive element in electrical communication with a plurality of control wires extending to the proximal end.

Example 41 is the direct visualization catheter of Example 36, wherein the adjustment mechanism includes a hinge coupled to the camera, a biasing element and an actuation rod. The actuation rod extends to the proximal end and is coupled to the hinge. The hinge is configured to permit the camera to move relative to the distal end of the elongate shaft. The biasing element is configured to apply a force about the hinge to bias the camera against the elongate shaft. The actuation rod is configured to extend a distal portion of the camera beyond the distal end of the elongate shaft such that the camera moves in a first direction when the actuation rod is pushed toward the distal end of the elongate shaft, and to retract the camera toward the proximal end of the elongate shaft when the actuation rod is pulled toward the proximal end of the elongate shaft such that the camera moves in a second direction.

Example 42 is the direct visualization catheter of any of Examples 37-41, wherein the hinge includes a plurality of electrical conductors configured to electrically connect the camera to electrical lines to be electrically connected to an image processing device for at least one of: image storage, image display, and image analysis.

Example 43 is the direct visualization catheter of Example 36, wherein the adjustment mechanism includes a ball and socket joint connecting the camera to the distal end of the elongate shaft, a helical spring connected to the ball and socket joint, and a torque shaft connected to the helical spring and extending to the proximal end to vary the viewing direction observed by the camera relative to the distal end of the elongate shaft.

Example 44 is a system for direct visualization within a blood pool. The system includes an image processing device and the direct visualization catheter according to any of Examples 36-43. The direct visualization device is electrically connected to the image processing device.

Example 45 is a direct visualization catheter including a handle, a transparent balloon, an elongate shaft having a proximal end and a distal end opposite the proximal end, and a camera assembly coupled the distal end of the elongate shaft and disposed within the balloon. The proximal end of the elongate shaft is coupled to the handle. The distal end of the elongate shaft is coupled to the balloon. The elongate shaft includes a plurality of lumens extending from the proximal end to the distal end. The camera assembly includes a camera, a hinge, a biasing element, and a control element. The hinge couples the camera to the elongate shaft at the distal end of the elongate shaft. The biasing element is configured to apply a first force about the hinge. The control element is configured to apply a second force about the hinge opposite the first force to vary a viewing direction observed by the camera relative to the distal end of the elongate shaft.

Example 46 is the direct visualization catheter of Example 45, wherein the control element includes an actuation thread extending through one of the plurality of lumens and a position switch disposed within the handle. The actuation thread physically connects the camera to the position switch.

Example 47 is the direct visualization catheter of Example 45, wherein the control element includes an inflatable device disposed between the elongate shaft and the camera and a pressure regulating device. One of the plurality of lumens fluidly connects the inflatable device to the pressure regulating device.

Example 48 is the direct visualization catheter of Example 45, wherein the control element includes an electroactive element disposed between the elongate shaft and the camera, a voltage regulating device, and control wires extending through at least one of the plurality of lumens. The control wires electrically connecting the electroactive element to the voltage regulating device.

Example 49 is the direct visualization catheter of Example 45, wherein the control element includes an actuation rod extending to the handle. The actuation rod is coupled to the hinge. The actuation rod is configured to extend a distal portion of the camera beyond the distal end of the elongate shaft when the actuation rod is pushed toward the distal end of the elongate shaft to permit the first force to move the camera in a first direction, and to retract the camera toward the proximal end of the elongate shaft when the actuation rod is pulled toward the proximal end of the elongate shaft and cause the camera to move in a second direction.

Example 50 is the direct visualization catheter of any of Examples 45-49, wherein the hinge includes a plurality of electrical conductors configured to electrically connect the camera to electrical lines to be electrically connected to an image processing device for at least one of: image storage, image display, and image analysis.

Example 51 is a direct visualization catheter including a handle, a balloon, an elongate shaft having a proximal end and a distal end opposite the proximal end, and a camera assembly. The proximal end of the elongate shaft is coupled to the handle. The distal end of the elongate shaft is coupled to the balloon. The camera assembly is coupled to the distal end of the elongate shaft and disposed within the balloon. The camera assembly includes a camera and an adjustment mechanism configured to vary a viewing direction observed by the camera relative to the distal end of the elongate shaft.

Example 52 is the direct visualization catheter of Example 51, wherein the adjustment mechanism includes a hinge coupling the camera to the distal end of the elongate shaft, a biasing element configured to apply a first force about the hinge, and a control element configured to apply a second force about the hinge opposite the first force. The hinge is configured to permit the camera to move relative to the distal end of the elongate shaft.

Example 53 is the direct visualization catheter of Example 52, wherein the control element includes an actuation thread extending to the handle, the actuation thread coupled to the camera.

Example 54 is the direct visualization catheter of Example 52, wherein the control element includes an inflatable device disposed between the distal end of the elongate shaft and the camera, the inflatable device in fluid communication with a pressurized control lumen extending to the handle.

Example 55 is the direct visualization catheter of Example 52, wherein the control element includes an electroactive element disposed between the distal end of the elongate shaft and the camera, the electroactive element in electrical communication with a plurality of control wires extending to the handle.

Example 56 is the direct visualization catheter of any of Examples 52-55, wherein the hinge includes a plurality of electrical conductors configured to electrically connect the camera to electrical lines to be electrically connected to an image processing device for at least one of: image storage, image display, and image analysis.

Example 57 is the direct visualization catheter of Example 51, wherein the adjustment mechanism includes a hinge coupled to the camera, a biasing element, and an actuation rod. The actuation rod is coupled to the hinge. The actuation rod extends to the proximal end of the elongate shaft. The hinge is configured to permit the camera to move relative to the distal end of the elongate shaft. The biasing element is configured to apply a force about the hinge to bias the camera against the elongate shaft. The actuation rod is configured to extend a distal portion of the camera beyond the distal end of the elongate shaft such that the camera moves in a first direction when the actuation rod is pushed toward the distal end of the elongate shaft, and to retract the camera toward the proximal end of the elongate shaft when the actuation rod is pulled toward the proximal end of the elongate shaft such that the camera moves in a second direction.

Example 58 is the direct visualization catheter of Example 51, wherein the adjustment mechanism includes a ball and socket joint connecting the camera to the distal end of the elongate shaft, a helical spring connected to the ball and socket joint, and a torque shaft connected to the helical spring to vary the viewing direction observed by the camera relative to the distal end of the elongate shaft.

Example 59 is a system for direct visualization within a blood pool. The system includes an image processing device and a direct visualization catheter electrically connected to the image processing device. The direct visualization catheter includes a handle, a transparent balloon, an elongate shaft, and a camera assembly. The elongate shaft has a proximal end and a distal end opposite the proximal end. The proximal end of the elongate shaft is coupled to the handle. The distal end of the elongate shaft is coupled to the balloon. The elongate shaft includes a plurality of lumens extending from the proximal end to the distal end. The camera assembly is coupled the distal end of the elongate shaft and disposed within the balloon. The camera assembly includes a camera, a hinge coupling the camera to the elongate shaft at the distal end of the elongate shaft, a biasing element configured to apply a first force about the hinge, and a control element configured to apply a second force about the hinge opposite the first force to vary a viewing direction observed by the camera relative to the distal end of the elongate shaft.

Example 60 is the system of Example 59, wherein the control element includes an actuation thread extending through one of the plurality of lumens and a position switch disposed within the handle, the actuation thread physically connecting the camera to the position switch.

Example 61 is the system of Example 59, wherein the control element includes an inflatable device disposed between the elongate shaft and the camera and a pressure regulating device. One of the plurality of lumens fluidly connects the inflatable device to the pressure regulating device.

Example 62 is the system of Example 59, wherein the control element includes an electroactive element disposed between the elongate shaft and the camera, a voltage regulating device, and control wires extending through at least one of the plurality of lumens. The control wires electrically connect the electroactive element to the voltage regulating device.

Example 63 is the system of Example 59, wherein the control element includes an actuation rod extending to the handle. The actuation rod is coupled to the hinge. The actuation rod is configured to extend a distal portion of the camera beyond the distal end of the elongate shaft when the actuation rod is pushed toward the distal end of the elongate shaft to permit the first force to move the camera in a first direction, and to retract the camera toward the proximal end of the elongate shaft when the actuation rod is pulled toward the proximal end of the elongate shaft and cause the camera to move in a second direction.

Example 64 is the system of any of Examples 59-63, wherein the hinge includes a plurality of electrical conductors configured to electrically connect the camera to electrical lines electrically connected to the image processing device for at least one of: image storage, image display, and image analysis.

Example 65 is a method for visualizing tissue within a body. The method includes inserting a catheter within the body, the catheter having a distal end and a proximal end opposite the distal end, inflating a transparent balloon at the distal end of the catheter, contacting the tissue to be visualized with a portion of the inflated balloon; and adjusting a viewing direction of a camera connected to the distal end of the catheter and disposed within the transparent balloon, the viewing direction variable relative to the distal end of the catheter.

Example 66 is the method of Example 65, wherein adjusting the viewing direction of the camera includes pulling an actuation thread connected to the camera to rotate the camera about a hinge coupling the camera to the catheter.

Example 67 is the method of Example 65, wherein adjusting the viewing direction of the camera includes inflating an inflatable device disposed between the camera and the catheter.

Example 68 is the method of Example 65, wherein adjusting the viewing direction of the camera includes varying a voltage applied to an electroactive element disposed between the camera and the catheter to rotate the camera about a hinge coupling the camera to the catheter.

Example 69 is the method of Example 65, wherein adjusting the viewing direction of the camera includes pushing on an actuation rod connected to the camera to extend a portion of the camera beyond the distal end of the catheter to permit the camera to rotate about a hinge coupling the camera to the catheter.

Example 70 is the method of Example 65, wherein adjusting the viewing direction of the camera includes rotating a torque shaft connected to a ball and socket joint connected to the camera.

While multiple examples are disclosed, still other examples in accordance with this disclosure will become apparent to those skilled in the art from the following detailed description, which shows and describes illustrative embodiments. Accordingly, the drawings and detailed description are to be regarded as illustrative in nature and not restrictive

BRIEF DESCRIPTION OF THE DRAWINGS

FIGS. 3A and 3B are side cross-sectional views of the distal end of the direct visualization catheter of FIG. 2, in accordance with some embodiments of this disclosure.

FIGS. 4A and 4B are side cross-sectional views of the distal end of another embodiment of the direct visualization catheter of FIG. 2, in accordance with some embodiments of this disclosure.

FIGS. 5A and 5B are side cross-sectional views of the distal end of another embodiment of the direct visualization catheter of FIG. 2, in accordance with some embodiments of this disclosure.

FIGS. 6A and 6B are side cross-sectional views of the distal end of another embodiment of the direct visualization catheter of FIG. 2, in accordance with some embodiments of this disclosure.

FIGS. 7A and 7B are side cross-sectional views of the distal end of another embodiment of the direct visualization catheter of FIG. 2, in accordance with some embodiments of this disclosure.

FIGS. 9A and 9B are side cross-sectional views of the distal end of another embodiment of the direct visualization catheter of FIG. 2, in accordance with some embodiments of this disclosure.

FIGS. 11A and 11B are side cross-sectional views of the distal end of another embodiment of the direct visualization catheter of FIG. 10, in accordance with some embodiments of this disclosure.

Figure 1:
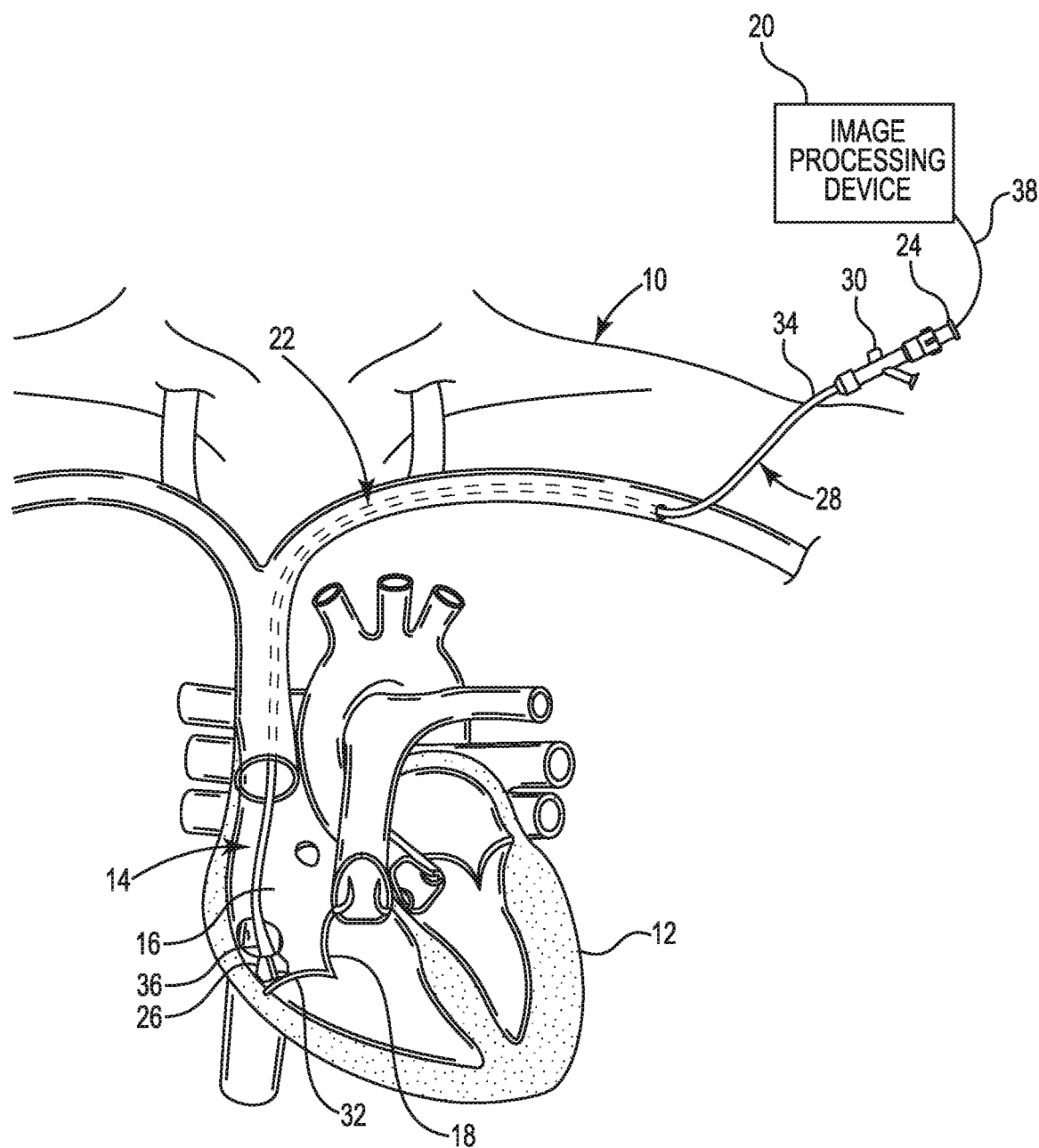
FIG. 1 is a schematic view illustrating in use of a system for direct visualization within a patient's heart, in accordance with embodiments of this disclosure.

While this disclosure is amenable to various modifications and alternative forms, specific embodiments have been shown by way of example in the drawings and are described in detail below. The intention, however, is not to limit the disclosure to the particular embodiments described. On the contrary, this disclosure is intended to cover all modifications, equivalents, and alternatives falling within the scope of the disclosure as defined by the appended claims.

DETAILED DESCRIPTION

Balloon catheters and systems and methods in accordance with embodiments of this disclosure can provide for direct visualization within a blood pool in a minimally-invasive manner. In some embodiments of this disclosure, an articulating camera disposed within a balloon at a distal end of a catheter can be configured for a low-profile delivery to the direct visualization site within the patient, and then the camera can be hinged away from the catheter in a deployed configuration. In the delivery configuration, the camera can be facing primarily in a radial direction. In the deployed, the camera can face primarily in an axial direction for effective viewing.

Such direct visualization catheters can have a smaller diameter during delivery. A smaller diameter catheter may case less distress to the patient when, for example, passing the catheter through the septum, from the right side of the heart to the left side of the heart. It is believed that causing less distress from the passing of the catheter through the septum may result in better patient outcomes.

In some other embodiments of this disclosure, an articulating camera disposed within a balloon at a distal end of a catheter can be aimed with an adjustment mechanism as described herein to vary a viewing direction observed by the camera relative to the catheter. By adjusting the viewing direction, navigation of the catheter can be enhanced and larger areas of tissue can be directly observed without having to move the catheter. It is believed that limiting the movement of the catheter may reduce any irritation caused by the catheter, resulting in better patient outcomes FIG. 1 is a schematic view illustrating in use of a system for direct visualization within a patient's heart, in accordance with embodiments of this disclosure. FIG. 1 illustrates a patient 10 including a heart 12 and a system 14 for direct visualization inserted into a right atrium 16 of the heart 12 for direct visualization of a tricuspid valve 18. As shown in FIG. 1, the system 14 can include an image processing device 20 and a direct visualization catheter 22. The image processing device 20 can include functionality for display of images, storage of images, and/or analysis of images. The catheter 22 can include a handle 24, a balloon 26, and an elongate shaft 28. The handle 24 can include an actuator 30 and a plurality of lumens (not shown). The balloon 26 can be formed of a transparent material and be a transparent balloon. In some embodiments, the balloon 26 can include a balloon lumen 32, as shown in FIG. 1. The elongate shaft 28 can be formed of a flexible, biocompatible polymer, such as, for example, silicone, polyisobutylene polyurethane, nylon, polyimide, polyetheretherketone, or a polyether block amide, such as Pebax® or Vestamid®. The elongate shaft 28 can include a proximal end 34 and a distal end 36 opposite the proximal end 34. The elongate shaft 28 can include a plurality of lumens (not shown) extending from the proximal end 34 to the distal end 36. The actuator 30 can be, for example, and without limitation, a position switch, a pressure regulating device, a voltage regulating device, or a lever or joy stick.

The catheter 22 can be electrically connected to the image processing device 20 by electrical lines 38. The proximal end 34 of the elongate shaft 28 can be coupled to the handle 24 with at least one of the plurality of lumens in the elongate shaft 28 connected with at least one of the plurality of lumens in the handle 24 to form a continuous lumen. The distal end 36 of the elongate shaft 28 can be coupled to the balloon 26 with the balloon lumen 32 connected with at least one of the plurality of lumens in the elongate shaft 28. So arranged, it is possible to pass devices, for example, a SpyBite® Biopsy Forceps from Boston Scientific Corporation, Natick, Mass., from the handle 24, through the elongate shaft 28, and out through the balloon 26.

In use, the actuator 30 on the handle 24 can adjust a viewing direction of an articulating camera assembly 40, not shown in FIG. 1, but describe in embodiments below. The articulating camera assembly 40 can be coupled to the distal end 36 of the elongate shaft 28. The articulating camera assembly 40 can be disposed within the balloon 26. The balloon 26 can be filled with a biocompatible, transparent fluid, such as saline solution, to displace blood adjacent to the tissues to be viewed. The transparent fluid can provide an optical lensing effect, further clarifying the view of the articulating camera assembly 40. Image output signals from the articulating camera assembly 40 can be sent to the image processing device 20 over the electrical lines 38. In some embodiments, the electrical lines 38 can also supply power from the image processing device 20 to the articulating camera assembly 40. In other embodiments, the electrical lines 38 can also connect to a separate power source to supply power to the articulating camera assembly 40.

Figure 2:
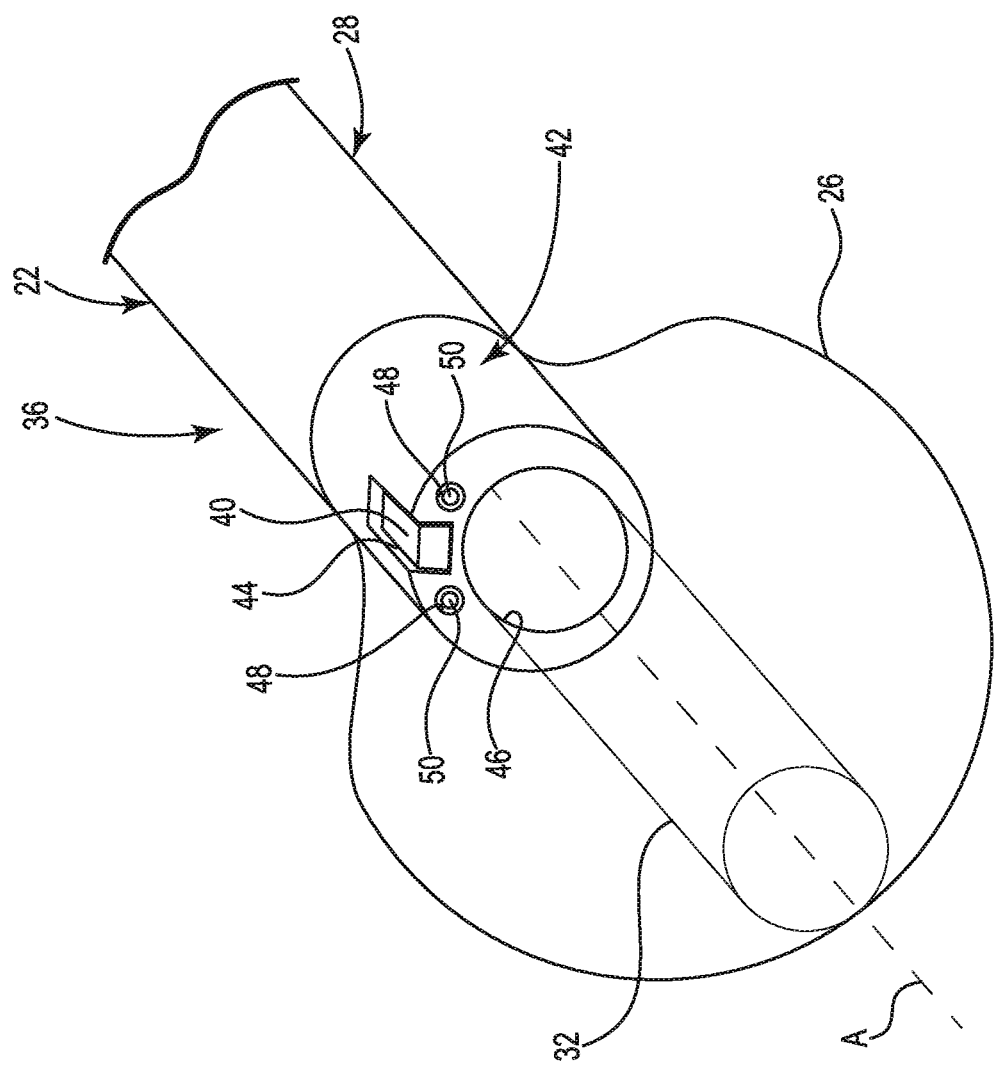
FIG. 2 is a perspective schematic view of a distal end of a direct visualization catheter, in accordance with embodiments of this disclosure.

FIG. 2 is a perspective schematic view of the distal end 36 of the direct visualization catheter 22, in accordance with some embodiments of this disclosure. The distal end 36 can define a longitudinal axis A. In some embodiments, the elongate shaft 28 can further include a cap 42 at the distal end 36, as shown in FIG. 2. The cap 42 can be formed of a variety of biocompatible materials that are typically harder than the flexible polymer of rest of the elongate shaft 28. Suitable materials for the cap 42 can include, for example, stainless steel, nickel-titanium alloys, cobalt based alloys (e.g., MP35N®), cobalt-chromium allows (e.g., Elgiloy®), and polymers such as polyetheretherketone, polyvinyl chloride, perfluoroalkoxy, polycarbonate, polyimide, polyethylene terephthalate, and polyetherimide. The cap 42 can include a slot 44, and plurality of lumens, such as delivery lumen 46, and at least one lighting lumen 48 (two shown) that align with corresponding lumens in the rest of the elongate shaft 28. The delivery lumen 46 is one of the plurality of lumens that extends from the distal end 36, through the elongate shaft 28, and into the handle 24. The delivery lumen 46 can be used to pass devices from the handle 24, through the elongate shaft 28, and out through the balloon lumen 32. In embodiments without a balloon lumen 32, the devices passed through the catheter 22 can penetrate the balloon 26. For clarity of illustration, the balloon lumen 32 is omitted from FIGS. 3A, 3B, 4A, 4B, 5A, 5B, 6A, 6B, 7A, 7B, 8A, 8B, 9A, 9B, and 11A, 11B. However, it is understood that all embodiments may include the balloon lumen 32.

The lighting lumen 48 can include a lighting device 50 (two shown). The lighting device 50 can include, for example and without limitation, a fiber optic cable or a light emitting diode. The lighting device 50 provides illumination for the articulating camera assembly 40. The balloon 26 can be attached around a circumference of the elongate shaft 28 by, for example, an adhesive. The balloon 26 can be attached to either or both of the cap 42 or a portion of the elongate shaft 28 adjacent to the cap 42. In some embodiments, the articulating camera assembly 40 can be disposed within the slot 44 to couple it to the distal end 36.

FIGS. 3A and 3B are side cross-sectional views of the distal end 36 of the direct visualization catheter 22 of FIG. 2, in accordance with embodiments of this disclosure. FIG. 3A shows the catheter 22 with the articulating camera assembly 40 in a delivery configuration. FIG. 3B shows the catheter 22 with the articulating camera assembly 40 in a deployed configuration. As shown in FIG. 3A, the articulating camera assembly 40 can include a camera 52 and an adjustment mechanism 54. The adjustment mechanism 54 can vary the direction faced by the camera 52 relative to the longitudinal axis A. In the embodiment shown in FIG. 3A, the adjustment mechanism 54 can include a hinge 56, a biasing element 58, and a control element 60. The plurality of lumens of the elongate shaft 28 can further include an inflation lumen 62 and a camera lumen 64. The inflation lumen 62 can extend to the handle 24 and on to a pressurized source of saline for inflation of the balloon 26 once the catheter 22 is positioned for viewing the heart 12 in the patient 10 (FIG. 1).

The camera 52 can include any type of solid state image sensor known in the art, for example and without limitation, a complementary metal-oxide-semiconductor (CMOS) image sensor or a charge-coupled device (CCD) image sensor. In some embodiments, the image sensor can be encased within a protective frame (not shown). The camera 52 can be relatively thin but with a relatively large image sensing area. That is, the camera 52 can be shaped like a plate with the image sensing area on a large side of the plate. The relatively large image sensing area can provide good quality imaging.

The hinge 56 is configured to permit the camera 52 to move relative to the distal end 36 of the elongate shaft 28. In some embodiments, the hinge 56 can be a multipart hinge including a hinge pin as is known in the art. The hinge can be formed of a biocompatible metal, such as stainless steel, or a biocompatible polymer, such as PEEK. One part of the hinge 56 can be coupled to the frame of the camera 52, while another part is coupled to a radially outward facing surface of the slot 44 to couple the camera 52 to the elongate shaft 28, as shown in FIG. 3A. The hinge 56 permits movement of the camera 52 relative to the distal end 36 of the elongate shaft 28 about an axis defined by the hinge pin.

In some other embodiments, the hinge 56 can include a hinge pin that extends through holes in the frame of the camera 52, the holes sized to permit free rotation of the frame relative to the pin. The pin can be formed of a biocompatible metal, such as stainless steel, or a biocompatible polymer, such as PEEK. The pin can be coupled on either end to opposite sidewalls of the slot 44 to connect the camera 52 to the elongate shaft 28 to permit movement of the camera 52 relative to the distal end 36 of the elongate shaft 28 about the hinge 56.

The biasing element 58 can be formed of any type of biocompatible elastic material, for example, and without limitation, nitinol, spring steel alloys (medical grade), and polymers, such as polyethylene terephthalate (e.g. Mylar®), poly(p-xylylene), amide polymers (e.g., Kevlar®), ultra-high-molecular-weight polyethylene, or nylon. The biasing element 58 can be configured as, for example, a helical coil spring, a leaf spring, or an elastic band. The biasing element 58 is configured with respect to the hinge 56 to provide a first force to maintain the hinge 56 in a fixed position in the absence of other forces.

In some other embodiments, the hinge 56 and the biasing element 58 can be integrated. For example, in some embodiments the hinge 56 can be in the form of a single L-shaped piece of biocompatible elastic material, such as those described above, thus integrating the hinge 56 and the biasing element 58. The first force of the elastic material can maintain the hinge 56/biasing element 58 in the L-shape in the absence of other forces.

The control element 60 can be configured to selectively apply a second force to the hinge 56 or to the camera 52 opposite the first force to counter the first force of the biasing element 58 and cause movement of the camera 52 relative to the distal end 36 of the elongate shaft 28. In some embodiments, the control element 60 includes an actuation thread coupled to the camera 52, as shown in FIG. 3A. The actuation thread is flexible and can be formed of, for example, a metal wire or a polymer thread made of, for example, amide polymers (e.g., Kevlar®), graphene, or nylon. The control element 60 can extend from the camera 52, through the camera lumen 64, and at least to the proximal end 34 of the elongate shaft 28. In the embodiment of FIG. 3A, the control element 60 extends to the actuator 30 on the handle 24 (FIG. 1). The actuator 30 can be a position switch that pulls on the control element 60 (actuation thread) to various extents depending on the position of the position switch. Thus, in the embodiment of FIG. 3A, the control element 60 (actuation thread) physically connects the actuator 30 (position switch) to the camera 52.

In some embodiments, the electrical lines 38 can extend from the camera 52, through the camera lumen 64, to the image processing device 20, as described above, to electrically connect the camera 52 to the image processing device 20. In some embodiments, the hinge 56 can be a conductive hinge that includes a plurality of electrical conductors configured to electrically connect the electrical lines 38 to the camera 52.

FIG. 3A shows the catheter 22 with the first force from the biasing element 58 applied to the hinge 56 and without the second force from the control element 60 being applied to the camera 52 so that the camera 52 faces in a primarily radial direction. For the purposes of this disclosure, the camera 52 faces in a primarily radial direction when it faces more in a radial direction relative to the longitudinal axis than in an axial direction relative to the longitudinal axis A.

In the embodiment shown in FIG. 3A, the camera 52 faces in a viewing direction V1. The viewing direction V1 is a completely radial inward direction toward the longitudinal axis A and does not face at all in the axial direction. So configured, the camera 52 has a low profile and does not extend beyond a diameter D1 of the elongate shaft 28.

As shown in FIG. 3A, in the delivery configuration, the camera 52 presents a small profile in the axial direction. This permits the diameter D1 of the elongate shaft 28 to be relatively small for ease of delivery and still accommodate the camera 52, while a diameter D2 of the delivery lumen 46 can be relatively large. For example, in some prior art direct visualization catheters in which a camera faces primarily axially during delivery, a 4 mm diameter (12 French) catheter is necessary to provide enough axially-facing space to accommodate the axially-facing camera and a 2.2 mm-2.5 mm diameter (7 French) delivery lumen. In contrast, in some embodiments of this disclosure, the diameter D1 of the elongate shaft 28 can be from 3.1 mm to 3.5 mm (10 French) while maintaining the lumen diameter D2 of the delivery lumen 46 at 2.2 mm to 2.5 mm.

Once the distal end 36 is delivered to the viewing site within the heart 12 of the patient 10 (FIG. 1), the articulated camera assembly 40 can be deployed, as shown in FIG. 3B. In FIG. 3B, the second force is applied to the camera 52 by moving the actuator 30 (FIG. 1) to pull the control element 60 (actuation thread). Pulling the control element 60 moves the camera 52 about the hinge 56 and against the biasing element 58 so that the camera 52 faces in a primarily axial direction. For the purposes of this disclosure, the camera 52 faces in a primarily axial direction when it faces more in the axial direction relative to the longitudinal axis than in the radial direction relative to the longitudinal axis A. In the embodiment shown in FIG. 3B, the camera 52 faces in a viewing direction V2. The viewing direction V2 is a completely axial direction toward and does not face at all in the radial direction. In the deployed configuration, the relatively large image sensing area of the camera 52 faces axially to provide high quality direct visualization of tissue.

As shown in FIG. 3B, in the deployed configuration the camera 52 extends radially beyond the elongate shaft 28. Once direct visualization of the tissue is completed, the actuator 30 (FIG. 1) can be moved to release the control element 60, permitting the biasing element 58 to move the camera 52 about the hinge 56 so that the camera 52 once again faces in the primarily radial direction and does not extend radially beyond the elongate shaft 28. In this way, the catheter 22 returns to a low-profile which may case less distress to the patient 10 when being removed from the patient 10.

FIGS. 4A and 4B are side cross-sectional views of the distal end 36 of another embodiment of the direct visualization catheter 22 of FIG. 2, in accordance with this disclosure. FIG. 4A shows the catheter 22 with the articulating camera assembly 40 in a delivery configuration. FIG. 4B shows the catheter 22 with the articulating camera assembly 40 in a deployed configuration. The embodiment shown in FIGS. 4A and 4B is substantially identical to that described above in reference to FIGS. 3A and 3B, except that the adjustment mechanism 54 includes a control element 160 instead of control element 60.

The control element 160 can include an inflatable device 162 and a pressurized control lumen 164. The inflatable device 162 is a balloon-like structure disposed between the cap 42 at the distal end 36 and the camera 52 such that inflation of the inflatable device 162 applies the second force to the camera 52 opposite the first force to counter the first force of the biasing element 58 and cause movement of the camera 52 relative to the distal end 36 of the elongate shaft 28. In some embodiments, the pressurized control lumen 164 can be a tube in fluid communication with the inflatable device 162 that extends from the inflatable device 162, through the camera lumen 64, and at least to the proximal end 34 of the elongate shaft 28. In the embodiment of FIG. 4A, the pressurized control lumen 164 extends to the actuator 30 on the handle 24 (FIG. 1). The actuator 30 can be a pressure regulating device that controls the pressure of a fluid in the pressurized control lumen 164 and the inflatable device 162 to various levels to increase or decrease the inflation of the inflatable device 162. In some embodiments, the fluid in the inflatable device 162 and the pressurized control lumen 164 is saline or helium.

FIG. 4A shows the catheter 22 with the first force from the biasing element 58 applied to the hinge 56 and without the second force from the control element 160 being applied to the camera 52 so that the camera 52 faces in a primarily radial direction. In the embodiment shown in FIG. 4A, the camera 52 faces in a viewing direction V3. The viewing direction V3 is a mostly radially outward direction away from the longitudinal axis A and faces the axial direction to a lesser extent than the radial direction. So configured, the camera 52 has a low profile and does not extend beyond a diameter D1 of the elongate shaft 28.

As shown in FIG. 4A, in the delivery configuration, the camera 52 presents a small profile in the axial direction. This permits the diameter D1 of the elongate shaft 28 to be relatively small for ease of delivery and still accommodate the camera 52, while a diameter D2 of the delivery lumen 46 can be relatively large, as described above in reference to the embodiment shown in FIG. 3A.

Once the distal end 36 is delivered to the viewing site within the heart 12 of the patient 10 (FIG. 1), the articulated camera assembly 40 can be deployed, as shown in FIG. 4B. In FIG. 4B, the second force is applied to the camera 52 by adjusting the actuator 30 (FIG. 1) to increase the pressure in the pressurized control lumen 164 and inflate the inflatable device 162. Inflating the inflatable device 162 moves the camera 52 about the hinge 56 and against the biasing element 58 so that the camera 52 faces a viewing direction V4. The viewing direction V4 is in a primarily axial direction. In the deployed configuration, the relatively large image sensing area of the camera 52 faces axially to provide high quality direct visualization of tissue.

As shown in FIG. 4B, in the deployed configuration the camera 52 extends radially beyond the elongate shaft 28. Once direct visualization of the tissue is completed, the actuator 30 (FIG. 1) can be adjusted to reduce the pressure in the pressurized control lumen 164 and deflate the inflatable device 162. As the inflatable device 162 deflates, the biasing element 58 to moves the camera 52 about the hinge 56 so that the camera 52 once again faces in the primarily radial direction and does not extend radially beyond the elongate shaft 28. In this way, the catheter 22 returns to a low-profile which may case less distress to the patient 10 when being removed from the patient 10 (FIG. 1).

FIGS. 5A and 5B are side cross-sectional views of the distal end 36 of another embodiment of the direct visualization catheter 22 of FIG. 2, in accordance with this disclosure. FIG. 5A shows the catheter 22 with the articulating camera assembly 40 in a delivery configuration. FIG. 5B shows the catheter 22 with the articulating camera assembly 40 in a deployed configuration. The embodiment shown in FIGS. 5A and 5B is substantially identical to that described above in reference to FIGS. 3A and 3B, except that the adjustment mechanism 54 includes a control element 260 instead of control element 60.

The control element 260 can include an electroactive element 262 and control wires 264. The electroactive element 262 may be formed of, for example, polyvinylidene fluoride, a ceramic piezoelectric compound, an ionic electroactive polymer, a dielectric electroactive polymer, a liquid crystal polymer, or a ferroelectric polymer. The electroactive element 262 is disposed between the cap 42 at the distal end 36 and the camera 52 such that when a voltage is applied to the electroactive element 262, the electroactive element 262 changes shape. The change in shape applies the second force to the camera 52 opposite the first force to counter the first force of the biasing element 58 and cause movement of the camera 52 relative to the distal end 36 of the elongate shaft 28. The control wires 264 can extend from electroactive element 262, through the camera lumen 64, and at least to the proximal end 34 of the elongate shaft 28. In the embodiment of FIG. 5A, the control wires 264 are in electrical communication with the electroactive element 262 and extend to the actuator 30 on the handle 24 (FIG. 1). The actuator 30 can be a voltage regulating device that controls the electric field applied to the control wires 264 and thus to the electroactive element 262 to change the shape of the electroactive element 262.

FIG. 5A shows the catheter 22 with the first force from the biasing element 58 applied to the hinge 56 and without the second force from the control element 260 being applied to the camera 52 so that the camera 52 faces in a primarily radial direction. In the embodiment shown in FIG. 5A, the camera 52 faces in a viewing direction V5. The viewing direction V5 is a mostly radially outward direction away from the longitudinal axis A and faces the axial direction to a lesser extent than the radial direction. So configured, the camera 52 has a low profile and does not extend beyond a diameter D1 of the elongate shaft 28.

As shown in FIG. 5A, in the delivery configuration, the camera 52 presents a small profile in the axial direction. This permits the diameter D1 of the elongate shaft 28 to be relatively small for ease of delivery and still accommodate the camera 52, while a diameter D2 of the delivery lumen 46 can be relatively large, as described above in reference to the embodiment shown in FIG. 3A.

Once the distal end 36 is delivered to the viewing site within the heart 12 of the patient 10 (FIG. 1), the articulated camera assembly 40 can be deployed, as shown in FIG. 5B. In FIG. 5B, the second force is applied to the camera 52 by adjusting the actuator 30 (FIG. 1) to increase the electric field applied to electroactive element 262. The increased electric field causes the electroactive element 262 to change shape, moving the camera 52 about the hinge 56 and against the biasing element 58 so that the camera 52 faces a viewing direction V6. The viewing direction V6 is in a primarily axial direction. In the deployed configuration, the relatively large image sensing area of the camera 52 faces axially to provide high quality direct visualization of tissue.

As shown in FIG. 5B, in the deployed configuration the camera 52 extends radially beyond the elongate shaft 28. Once direct visualization of the tissue is completed, the actuator 30 (FIG. 1) can be adjusted to decrease the electric field applied to electroactive element 262. The decreased electric field causes the electroactive element 262 to change shape, permitting the biasing element 58 to move the camera 52 about the hinge 56 so that the camera 52 once again faces in the primarily radial direction and does not extend radially beyond the elongate shaft 28. In this way, the catheter 22 returns to a low-profile which may case less distress to the patient 10 when being removed from the patient 10.

FIGS. 6A and 6B are side cross-sectional views of the distal end 36 of the direct visualization catheter 22 of FIG. 2, in accordance with some embodiments of this disclosure. FIG. 6A shows the catheter 22 with the articulating camera assembly 40 having a viewing direction $V_1$. FIG. 6B shows the catheter 22 with the articulating camera assembly 40 having a viewing direction $V_2$ that is different from viewing direction $V_1$. As shown in FIG. 6A, the articulating camera assembly 40 can include a camera 352 and an adjustment mechanism 354. The adjustment mechanism 354 can vary the viewing direction observed by the camera 352 relative to the distal end 36. In the embodiment shown in FIG. 6A, the adjustment mechanism 354 can include a hinge 356, a biasing element 358, and a control element 360. The plurality of lumens of the elongate shaft 28 can further include an inflation lumen 362 and a camera lumen 364. The inflation lumen 362 can extend to the handle 24 and on to a pressurized source of saline for inflation of the balloon 26 once the catheter 22 is positioned for viewing in the heart 12 of the patient 10 (FIG. 1).

The camera 352 can include any type of solid state image sensor known in the art, for example and without limitation, a complementary metal-oxide-semiconductor (CMOS) image sensor or a charge-coupled device (CCD) image sensor. In some embodiments, the image sensor can be encased within a protective box, or frame.

The hinge 356 is configured to permit the camera 352 to move relative to the distal end 36 of the elongate shaft 28. In some embodiments, the hinge 356 can be a multipart hinge including a hinge pin as is known in the art. The hinge 356 can be formed of a biocompatible metal, such as stainless steel, or a biocompatible polymer, such as PEEK. One part of the hinge 356 can be coupled to the camera 352, while another part is coupled to a radially outward facing surface of the slot 44 to couple the camera 352 to the elongate shaft 28, as shown in FIG. 6A. The hinge 356 permits movement of the camera 352 relative to the distal end 36 of the elongate shaft 28 about an axis defined by the hinge pin.

In some other embodiments, the hinge 356 can include a hinge pin that extends through holes in the frame of the camera 352, the holes sized to permit free rotation of the frame relative to the pin. The pin can be formed of a biocompatible metal, such as stainless steel, or a biocompatible polymer, such as PEEK. The pin can be coupled on either end to opposite sidewalls of the slot 44 to connect the camera 352 to the elongate shaft 28 to permit movement of the camera 352 relative to the distal end 36 of the elongate shaft 28 about the hinge 356.

The biasing element 358 can be formed of any type of biocompatible elastic material, for example, and without limitation, nitinol, spring steel alloys (medical grade), and polymers, such as polyethylene terephthalate (e.g. Mylar®), poly(p-xylylene), amide polymers (e.g., Kevlar®), ultra-high-molecular-weight polyethylene, or nylon. The biasing element 358 can be configured as, for example, a helical coil spring, a leaf spring, or an elastic band. The biasing element 358 is configured with respect to the hinge 356 to provide a first force to maintain the hinge 356 in a fixed position in the absence of other forces.

In some other embodiments, the hinge 356 and the biasing element 358 can be integrated. For example, in some embodiments the hinge 356 can be in the form of a single L-shaped piece of biocompatible elastic material, such as those described above, thus integrating the hinge 356 and the biasing element 358. The first force of the elastic material can maintain the hinge 356/biasing element 358 in the L-shape in the absence of other forces.

The control element 360 can be configured to selectively apply a second force to the hinge 356 or to the camera 352 opposite the first force to counter the first force of the biasing element 358 and cause movement of the camera 352 relative to the distal end 36 of the elongate shaft 28. In some embodiments, the control element 360 includes an actuation thread coupled to the camera 352, as shown in FIG. 6A. The actuation thread is flexible and can be formed of, for example, a metal wire or a polymer thread made of, for example, amide polymers (e.g., Kevlar®), graphene, or nylon. The control element 360 can extend from the camera 352, through the camera lumen 364, and at least to the proximal end 34 of the elongate shaft 28. In the embodiment of FIG. 6A, the control element 360 extends to the actuator 30 on the handle 24 (FIG. 1). The actuator 30 can be a position switch that pulls on the control element 360 (actuation thread) to various extents depending on the position of the position switch. Thus, in the embodiment of FIG. 6A, the control element 360 (actuation thread) physically connects the actuator 30 (position switch) to the camera 352.

In some embodiments, the electrical lines 38 can extend from the camera 352, through the camera lumen 364, to the image processing device 20, as described above, to electrically connect the camera 352 to the image processing device 20. In some embodiments, the hinge 356 can be a conductive hinge that includes a plurality of electrical conductors configured to electrically connect the electrical lines 38 to the camera 352.

FIG. 6A shows the catheter 22 with the first force from the biasing element 358 applied to the hinge 356 and without the second force from the control element 360 being applied to the camera 352 so that the camera 352 has a viewing direction $V_1$ as shown. In FIG. 6B, the second force is applied to the camera 352 by moving the actuator 30 (FIG. 1) to pull the control element 360 (actuation thread). Pulling the control element 360 moves the camera 352 about the hinge 356 and against the biasing element 358 to change the viewing direction to the viewing direction $V_2$, which is different from the viewing direction $V_1$. In this way, the viewing angle or direction of the camera 352 may be varied by adjusting the actuator 30 (position switch) to pull the control element 360 to varying extents.

In some embodiments according to FIGS. 6A and 6B, the viewing direction $V_2$ can form an angle C with respect to the viewing direction $V_1$ that can be as small as 1°, 5°, 10°, 20°, 30°, or 40°, or as large as 50°, 60°, 70°, 80°, 85°, or 89°, or between any two of the preceding angles. For example, in some embodiments, the angle C can range from 1° to 89°, 5° to 85°, 10° to 80°, 20° to 70°, 30° to 60°, or 40° to 50°. For the purposes of this disclosure, the angle C is positive when the viewing direction $V_2$ is directed radially outward relative to the viewing direction $V_1$, as shown in FIG. 6B, and the angle C is negative when the viewing direction $V_2$ is directed radially inward relative to the viewing direction $V_1$, as shown in FIG. 9B described below.

FIGS. 7A and 7B are side cross-sectional views of the distal end 36 of another embodiment of the direct visualization catheter 22 of FIG. 2, in accordance with this disclosure. FIG. 7A shows the catheter 22 with the articulating camera assembly 40 having a viewing direction $V_1$. FIG. 7B shows the catheter 22 with the articulating camera assembly 40 having a viewing direction $V_2$ that is different from viewing direction $V_1$. The embodiment shown in FIGS. 7A and 7B is substantially identical to that described above in reference to FIGS. 6A and 6B, except that the adjustment mechanism 354 includes a control element 460 instead of control element 360.

The control element 460 can include an inflatable device 462 and a pressurized control lumen 464. The inflatable device 462 is a balloon-like structure disposed between the cap 42 at the distal end 36 and the camera 352 such that inflation of the inflatable device 462 applies the second force to the camera 352 opposite the first force to counter the first force of the biasing element 358 and cause movement of the camera 352 relative to the distal end 36 of the elongate shaft 28. In some embodiments, the pressurized control lumen 464 can be a tube in fluid communication with the inflatable device 462 that extends from the inflatable device 462, through the camera lumen 364, and at least to the proximal end 34 of the elongate shaft 28. In the embodiment of FIG. 7A, the pressurized control lumen 464 extends to the actuator 30 on the handle 24 (FIG. 1). The actuator 30 can be a pressure regulating device that controls the pressure of a fluid in the pressurized control lumen 464 and the inflatable device 462 to various levels to increase or decrease the inflation of the inflatable device 462. In some embodiments, the fluid in the inflatable device 462 and the pressurized control lumen 464 is saline or helium.

FIG. 7A shows the catheter 22 with the first force from the biasing element 358 applied to the hinge 356 and without the second force from the control element 460 being applied to the camera 352 so that the camera 352 has a viewing direction $V_1$ as shown. In FIG. 7B, the second force is applied to the camera 352 by adjusting the actuator 30 (FIG. 1) to increase the pressure in the pressurized control lumen 464 and inflate the inflatable device 462. Inflating the inflatable device 462 moves the camera 352 about the hinge 356 and against the biasing element 358 to change the viewing direction to the viewing direction $V_2$, which is different from the viewing direction $V_1$. In this way, the viewing angle or direction of the camera 352 may be varied by adjusting the actuator 30 (pressure regulating device) to inflate the inflatable device 462 to varying extents.

In some embodiments according to FIGS. 7A and 7B, the viewing direction $V_2$ can form an angle C with respect to the viewing direction $V_1$ that can be as small as 1°, 5°, 10°, 20°, 30°, or 40°, or as large as 50°, 60°, 70°, 80°, 85°, or 89°, or between any two of the preceding angles. For example, in some embodiments, the angle C can range from 1° to 89°, 5° to 85°, 10° to 80°, 20° to 70°, 30° to 60°, or 40° to 50°.

Figure 8A:
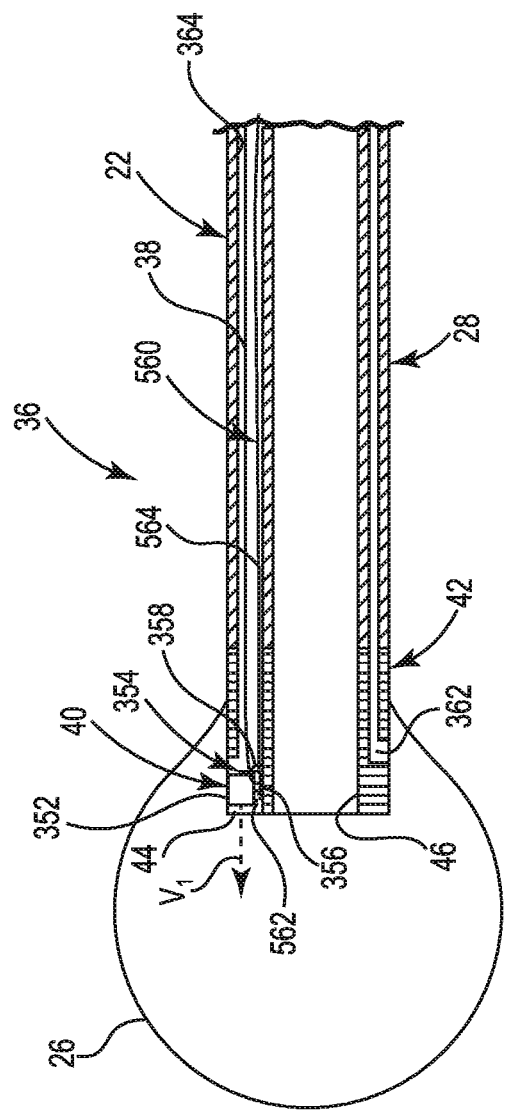
FIGS. 8A and 8B are side cross-sectional views of the distal end of another embodiment of the direct visualization catheter of FIG. 2, in accordance with some embodiments of this disclosure.
Figure 8B:
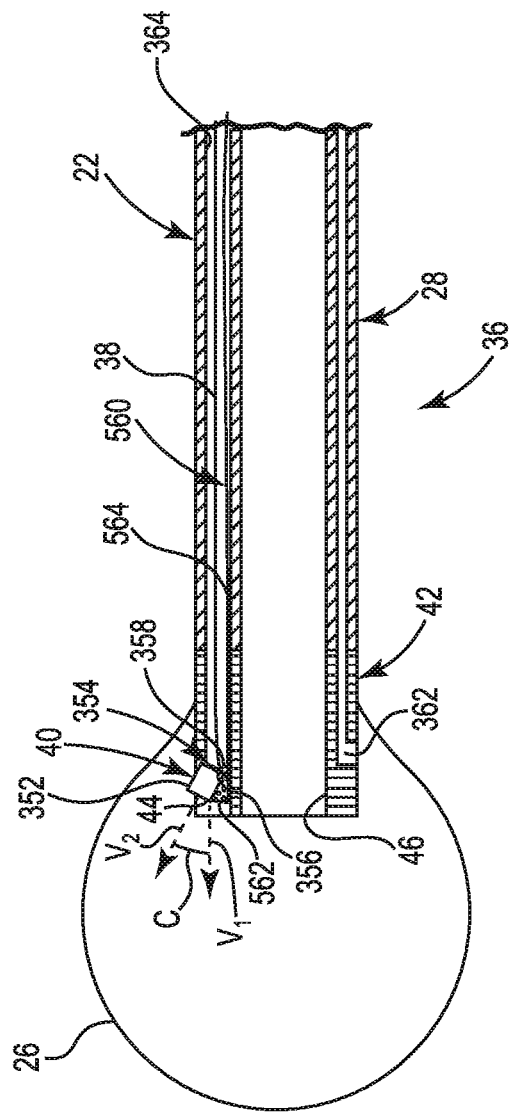

FIGS. 8A and 8B are side cross-sectional views of the distal end 36 of another embodiment of the direct visualization catheter 22 of FIG. 2, in accordance with this disclosure. FIG. 8A shows the catheter 22 with the articulating camera assembly 40 having a viewing direction $V_1$. FIG. 8B shows the catheter 22 with the articulating camera assembly 40 having a viewing direction $V_2$ that is different from viewing direction $V_1$. The embodiment shown in FIGS. 8A and 8B is substantially identical to that described above in reference to FIGS. 6A and 6B, except that the adjustment mechanism 354 includes a control element 560 instead of control element 360.

The control element 560 can include an electroactive element 562 and control wires 564. The electroactive element 562 may be formed of, for example, polyvinylidene fluoride, a ceramic piezoelectric compound, an ionic electroactive polymer, a dielectric electroactive polymer, a liquid crystal polymer, or a ferroelectric polymer. The electroactive element 562 is disposed between the cap 42 at the distal end 36 and the camera 352 such that when a voltage is applied to the electroactive element 562, the electroactive element 562 changes shape. The change in shape applies the second force to the camera 352 opposite the first force to counter the first force of the biasing element 358 and cause movement of the camera 352 relative to the distal end 36 of the elongate shaft 28. The control wires 564 can extend from electroactive element 562, through the camera lumen 364, and at least to the proximal end 34 of the elongate shaft 28. In the embodiment of FIG. 8A, the control wires 564 are in electrical communication with the electroactive element 562 and extend to the actuator 30 on the handle 24 (FIG. 1). The actuator 30 can be a voltage regulating device that controls the electric field applied to the control wires 564 and thus to the electroactive element 562 to change the shape of the electroactive element 562.

FIG. 8A shows the catheter 22 with the first force from the biasing element 358 applied to the hinge 356 and without the second force from the control element 560 being applied to the camera 352 so that the camera 352 has a viewing direction $V_1$ as shown. In FIG. 8B, the second force is applied to the camera 352 by adjusting the actuator 30 (FIG. 1) to increase the electric field applied to electroactive element 562. The increased electric field causes the electroactive element 562 to change shape, moving the camera 352 about the hinge 356 and against the biasing element 358 to change the viewing direction to the viewing direction $V_2$, which is different from the viewing direction $V_1$. In this way, the viewing angle or direction of the camera 352 may be varied by adjusting the actuator 30 (voltage regulating device) to change the shape of the electroactive element 562 to varying extents.

In some embodiments according to FIGS. 8A and 8B, the viewing direction $V_2$ can form an angle C with respect to the viewing direction $V_1$ that can be as small as 1°, 5°, 10°, 20°, 30°, or 40°, or as large as 50°, 60°, 70°, 80°, 85°, or 89°, or between any two of the preceding angles. For example, in some embodiments, the angle C can range from 1° to 89°, 5° to 85°, 10° to 80°, 20° to 70°, 30° to 60°, or 40° to 50°.

FIGS. 9A and 9B are side cross-sectional views of the distal end 36 of another embodiment of the direct visualization catheter 22 of FIG. 2, in accordance with this disclosure. FIG. 9A shows the catheter 22 with the articulating camera assembly 40 having a viewing direction $V_1$. FIG. 9B shows the catheter 22 with the articulating camera assembly 40 having a viewing direction $V_2$ that is different from viewing direction $V_1$. The embodiment shown in FIGS. 9A and 9B can be substantially identical to that described above in reference to FIGS. 6A and 6B, except that the control element 360 is replaced by an actuation rod 660 and the hinge 356 is free to slide along the radially outward facing surface of the slot 44. In some embodiments, in which the hinge 356 includes a hinge pin, the hinge pin may ride in recesses (not shown) on opposite facing sides of the slot 44.

In contrast to control element 360 in which the actuation thread is coupled to the camera 352, the actuation rod 660 is coupled to the hinge 356. The actuation rod 660 can extend from the hinge 356, through the camera lumen 364, and at least to the proximal end 34 of the elongate shaft 28. In the embodiment of FIG. 9A, the actuation rod 660 extends to the actuator 30 on the handle 24 (FIG. 1). The actuator 30 can be a position switch that pushes on or pulls on the actuation rod 660 to various extents depending on the position of the position switch. Thus, in the embodiment of FIG. 9A, the actuation rod 660 physically connects the actuator 30 (position switch) to the hinge 356. The actuation rod 660 can be a flexible rod or tube. In some embodiments, the actuation rod 660 and can be formed as a slotted tube or a multi-filar coiled spring. In some embodiments, the actuation rod 660 can be made out of, for example, nickel-titanium alloys, MP35N®, steel alloys (medical grade), or alloys of cobalt and chromium. The actuation rod 660 can be stiffer than the actuation thread of the control element 360.

FIG. 9A shows the catheter 22 with the biasing element 358 applying a first force about the hinge 356 to bias the camera 352 against the radially outward facing surface of the slot 44 of cap 42 of the elongate shaft 28 so that the camera 352 has a viewing direction $V_1$ as shown. In FIG. 9B, the actuation rod 660 is pushed by adjusting the actuator 30 (FIG. 1) to extend at least a distal portion of the camera 352 beyond the distal end 36 of the elongate shaft 28, permitting the camera 352 to move in a first direction $B_1$ to change the viewing direction to the viewing direction $V_2$. Adjusting the actuator 30 again to pull on the actuation rod 660 retracts the camera 352 toward the proximal end 34 (FIG. 1) of the elongate shaft 28. Pulling the camera 352 back against the cap 42 applies a second force about the hinge 356 to counter the first force, moving the camera 352 in a second direction $B_2$ and back to the viewing direction $V_1$ as shown in FIG. 9A. In this way, the viewing angle or direction of the camera 352 may be varied by adjusting the actuator 30 (position switch) to push or pull the actuation rod 660 to varying extents.

In some embodiments according to FIGS. 9A and 9B, the viewing direction $V_2$ can form an angle C with respect to the viewing direction $V_1$ that can be as small as −1°, −5°, −10°, −20°, −30°, or −40°, or as large as −50°, −60°, −70°, −80°, −85° or −89°, or between any two of the preceding angles. For example, in some embodiments, the angle C can range from −1° to −89°, −5° to −85°, −10° to −80°, −20° to −70°, −30° to −60°, or −40° to −50°.

Figure 10:
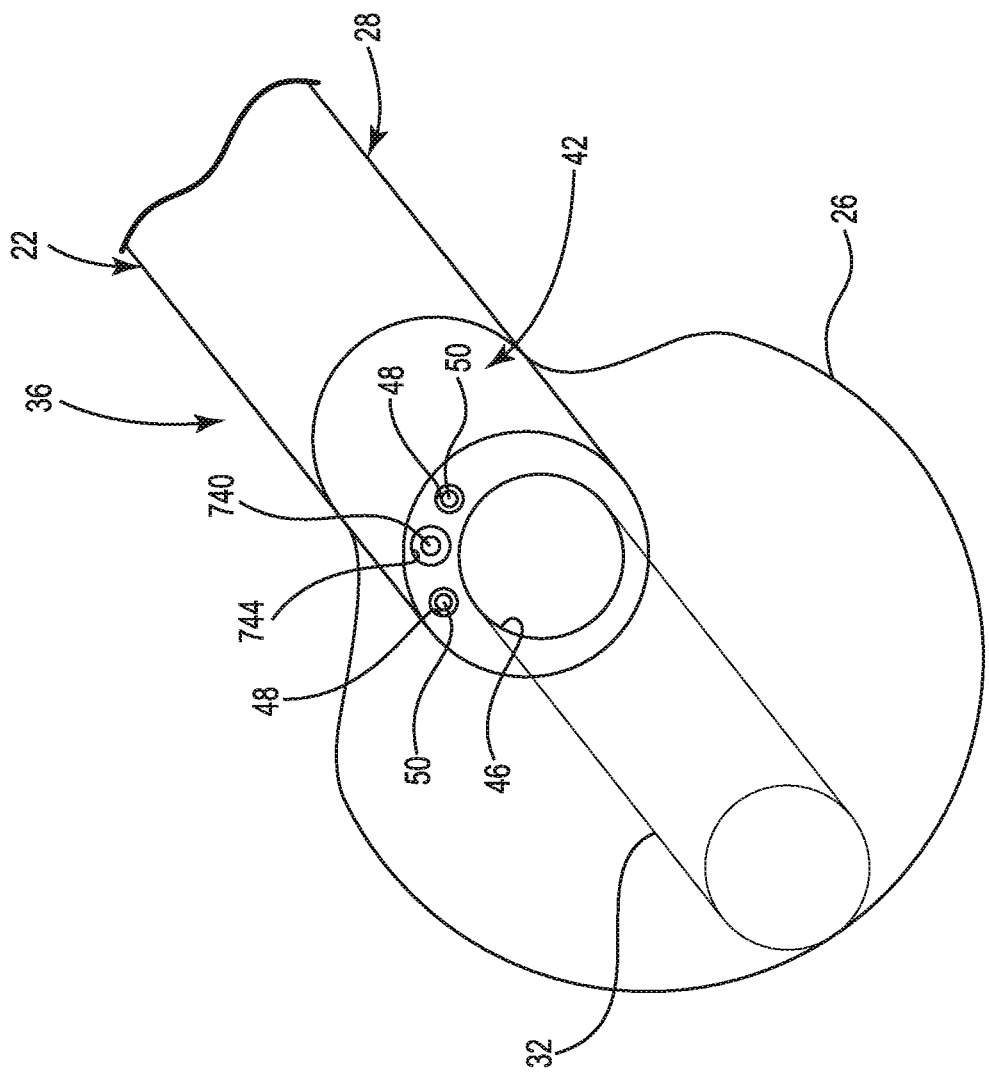
FIG. 10 is a perspective schematic view of a distal end portion of another direct visualization catheter, in accordance with some embodiments of this disclosure.

FIG. 10 is a perspective schematic view of the distal end 36 of the direct visualization catheter 22, in accordance with embodiments of this disclosure. The embodiment of FIG. 10 is substantially identical to the embodiment of FIG. 2, except that the articulating camera assembly 40 is replaced by an articulating camera assembly 740, and the slot 44 and the camera lumen 364 are replaced by a camera lumen 744. The articulating camera assembly 740 can be disposed within the camera lumen 744 to couple it to the distal end 36.

FIGS. 11A and 11B are side cross-sectional views of the distal end 36 of the direct visualization catheter 22 of FIG. 10, in accordance with embodiments of this disclosure. FIG. 11A shows the catheter 22 with the articulating camera assembly 740 having a viewing direction $V_1$. FIG. 11B shows the catheter 22 with the articulating camera assembly 740 having a viewing direction $V_2$ that is different from viewing direction $V_1$. As shown in FIG. 11A, the articulating camera assembly 740 can include a camera 352 and an adjustment mechanism 754. The adjustment mechanism 754 can vary the viewing direction observed by the camera 352 relative to the distal end 36. In the embodiment shown in FIG. 11A, the adjustment mechanism 754 can include ball and socket joint 756, a helical spring 758, and a torque shaft 760.

The ball and socket joint 756 can be primarily disposed within the camera lumen 744 with a portion of the ball and socket joint 756 projecting out of the camera lumen 744 at the distal end 36. The camera 352 can be connected to the portion of the ball and socket joint 756 projecting out of the camera lumen 744. The helical spring 758 can be connected to the ball and socket joint 756 within the camera lumen 744. The torque shaft 760 can be connected to an end of the helical spring 758 opposite the ball and socket joint 756. The torque shaft 760 can be a flexible rod or tube. In some embodiments, the torque shaft 760 and can be formed as a slotted tube or a multi-filar coiled spring. In some embodiments, the torque shaft 760 can be made out of, for example, nickel-titanium alloys, MP35N®, steel alloys (medical grade), or alloys of cobalt and chromium. The torque shaft 760 can extend from the helical spring 758, through the camera lumen 744, and at least to the proximal end 34 of the elongate shaft 28 (FIG. 1). In the embodiment of FIG. 11A, the torque shaft 760 extends to the actuator 30 on the handle 24 (FIG. 1). The actuator 30 can be a lever or joy stick that rotates the torque shaft 760 to various extents depending on the position of the lever or joy stick.

FIG. 11A shows the catheter 22 with the ball and socket joint 756 positioned by the actuator 30 so that the camera 352 has a viewing direction $V_1$ as shown. In FIG. 11B, the ball and socket joint 756 is positioned by the actuator 30 rotating the torque shaft 760, which rotates the helical spring 758 to move adjust the ball and socket joint 756 so that the camera 352 has a viewing direction $V_2$, which is different from the viewing direction $V_1$. In this way, the viewing angle or direction of the camera 352 may be varied by adjusting the actuator 30 (lever or joy stick) to rotate the torque shaft 760 to varying extents.

In some embodiments according to FIGS. 11A and 11B, the viewing direction $V_2$ can form an angle C with respect to the viewing direction $V_1$ that can be as small as −1°, −5°, −10°, −20°, −30°, or −40°, or as large as −50°, −60°, −70°, −80°, −85°, or −89°, or between any two of the preceding angles. For example, in some embodiments, the angle C can range from −1° to −89°, −5° to −85°, −10° to −80°, −20° to −70°, −30° to −60°, or −40° to −50°. In other embodiments according to FIGS. 11A and 11B, the viewing direction $V_2$ can form an angle C with respect to the viewing direction $V_1$ that can be as small as 1°, 5°, 10°, 20°, 30°, or 40°, or as large as 50°, 60°, 70°, 80°, 85°, or 89°, or between any two of the preceding angles. For example, in some embodiments, the angle C can range from 1° to 89°, 5° to 85°, 10° to 80°, 20° to 70°, 30° to 60°, or 40° to 50°. In some further embodiments according to FIGS. 11A and 11B, the viewing direction $V_2$ can form an angle C with respect to the viewing direction $V_1$ that can range from −89° to 89°, −85° to 85°, −80° to 80°, −70° to 70°, −60° to 60°, −50° to 50°, −40° to 40°, −30° to 30°, −20° to 20°, −10° to 10°, or −5° to 5°.

Various modifications and additions can be made to the embodiments discussed without departing from the scope of this disclosure. For example, while the embodiments described above refer to particular features, the scope of this disclosure also includes embodiments having different combinations of features and embodiments that do not include all of the described features. Accordingly, the scope of this disclosure is intended to embrace all such alternatives, modifications, and variations as fall within the scope of the claims, together with all equivalents thereof.

We claim:

1. A direct visualization catheter comprising:
    a handle;
    a balloon;
    an elongate shaft having a proximal end and a distal end opposite the proximal end, the proximal end coupled to the handle, the distal end coupled to the balloon and defining a longitudinal axis; and
    a camera assembly coupled to the distal end of the elongate shaft and disposed within the balloon, the camera assembly including:
    a camera; and
    an adjustment mechanism for varying a configuration of the camera relative to the distal end of the elongate shaft between a delivery configuration and a deployed configuration, the camera facing primarily in a radial direction in the delivery configuration and the camera facing primarily in an axial direction in the deployed configuration;

wherein the adjustment mechanism includes:
a hinge coupling the camera to the distal end of the elongate shaft, the hinge configured to permit the camera to move relative to the distal end of the elongate shaft;
a biasing element configured to apply a first force about the hinge and arranged such that the camera is biased about the hinge in the delivery configuration to thereby bias a viewing direction of the camera radially inward toward the longitudinal axis.

2. The direct visualization catheter of claim 1, wherein in the delivery configuration, the camera does not extend radially beyond the elongate shaft, and in the deployed configuration, the camera extends radially beyond the elongate shaft.

3. The direct visualization catheter of claim 1, wherein the elongate shaft has a diameter from 3.1 mm to 3.5 mm, the elongate shaft further including a lumen extending from the proximal end to the distal end, the lumen having a lumen diameter from 2.2 mm to 2.5 mm.

4. The direct visualization catheter of claim 1, wherein the adjustment mechanism further includes a control element configured to apply a second force about the hinge opposite the first force.

5. The direct visualization catheter of claim 4, wherein the control element includes an actuation thread extending to the handle, the actuation thread coupled to the camera.

6. A system for direct visualization within a blood pool, the system comprising:
an image processing device; and
a direct visualization catheter electrically connected to the image processing device, the direct visualization catheter including:
a handle;
a transparent balloon;
an elongate shaft having a proximal end and a distal end opposite the proximal end, the proximal end coupled to the handle, the distal end coupled to the balloon and defining a longitudinal axis, the elongate shaft including a plurality of lumens extending from the proximal end to the distal end; and
a camera assembly coupled the distal end of the elongate shaft and disposed within the balloon, the camera assembly including:
a camera;
a hinge connecting the camera to the elongate shaft at the distal end of the elongate shaft;
a biasing element configured to apply a first force about the hinge and arranged such that the camera is biased about the hinge in the delivery configuration to thereby bias a viewing direction of the camera radially inward toward the longitudinal axis; and
a control element configured to apply a second force about the hinge opposite the first force to vary a configuration of the camera relative to the distal end of the elongate shaft between a delivery configuration and a deployed configuration, the camera facing primarily in a radial direction in the delivery configuration and the camera facing primarily in an axial direction in the deployed configuration.

7. The system of claim 6, wherein the control element includes:
an actuation thread extending through one of the plurality of lumens; and
a position switch disposed within the handle, the actuation thread physically connecting the camera to the position switch.

8. The system of claim 6, wherein the hinge includes a plurality of electrical conductors configured to electrically connect the camera to electrical lines electrically connected to the image processing device for at least one of: image storage, image display, and image analysis.

9. The system of claim 6, wherein in the delivery configuration, the camera does not extend radially beyond the elongate shaft, and in the deployed configuration, the camera extends radially beyond the elongate shaft.

10. The system of claim 6, wherein the elongate shaft has a diameter from 3.1 mm to 3.5 mm and one of the plurality of lumens has a lumen diameter from 2.2 mm to 2.5 mm.

11. A method for visualizing tissue within a body, the method comprising:
inserting a catheter within the body, the catheter having a proximal end and a distal end opposite the proximal end, the distal end defining a longitudinal axis;
inflating a transparent balloon at the distal end of the catheter;
adjusting a configuration of a camera between a delivery configuration and a deployed configuration, the camera facing primarily in a radial direction in the delivery configuration and the camera facing primarily in an axial direction in the deployed configuration, the camera connected to the distal end of the catheter such that the camera is biased, via a biasing member, in the delivery configuration with a viewing direction of the camera facing radially inward toward the longitudinal axis and disposed within the transparent balloon; and
contacting the tissue to be visualized with a portion of the inflated balloon.

12. The method of claim 11, wherein adjusting the configuration of the camera between the delivery configuration and the deployed configuration includes pulling an actuation thread connected to the camera to move the camera about a hinge connecting the camera to the catheter.

13. The method of claim 11, wherein in the delivery configuration, the camera does not extend radially beyond the catheter, and in the deployed configuration, the camera extends radially beyond the catheter.

* * * * *